United States Patent [19]
Ryder

[11] Patent Number: 5,797,389
[45] Date of Patent: Aug. 25, 1998

[54] VARIABLE OXYGEN CONCENTRATION HIGH-FLOW NEBULIZER

[76] Inventor: Steven L. Ryder, 2460 Hartford Ave., Fullertown, Calif. 92835

[21] Appl. No.: 706,943

[22] Filed: Sep. 3, 1996

Related U.S. Application Data

[63] Continuation-in-part of Ser. No. 524,278, Sep. 6, 1995, abandoned.

[51] Int. Cl.$^6$ ................................................. A61M 11/02
[52] U.S. Cl. .............................. 128/200.21; 128/205.11
[58] Field of Search ..................... 128/200.18, 200.19, 128/200.21, 203.12, 203.16, 203.17, 203.24, 203.25, 204.29, 205.11; 239/338; 137/837, 838

[56] References Cited

U.S. PATENT DOCUMENTS

| | | | |
|---|---|---|---|
| 3,915,386 | 10/1975 | Vora | 128/200.28 |
| 5,322,057 | 6/1994 | Raabe et al. | 128/203.12 |

FOREIGN PATENT DOCUMENTS

| | | | |
|---|---|---|---|
| 0 261 649 | 3/1988 | European Pat. Off. | |
| 542908 | 8/1922 | France | |
| 674229 | 1/1930 | France | |

*Primary Examiner*—Mickey Yu
*Assistant Examiner*—William J. Deane, Jr.
*Attorney, Agent, or Firm*—Swanson & Bratschun LLC

[57] ABSTRACT

A nebulizer (10) for providing a select oxygen concentration and total flow of respiratory gas includes at least two oxygen nozzles (102, 104, 106, 108), each oxygen nozzle having an outlet. A pressurized oxygen supply is connected in fluid communication to each nozzle. A liquid outlet (80) corresponding to each nozzle (102, 104, 106, 108) is positioned proximate the nozzle outlet of the corresponding nozzle for nebulization of liquid from the liquid outlet (80) in a stream of oxygen flowing from the gas outlet of each nozzle (102, 104, 106, 108). A liquid supply (174) is connected in liquid communication to each liquid outlet (80). An oxygen adjustment mechanism is provided in fluid communication with at least one of the oxygen nozzles (102, 104, 106, 108) for selectively recruiting the at least one oxygen nozzle and preventing gas from flowing from the at least one oxygen nozzle.

32 Claims, 18 Drawing Sheets

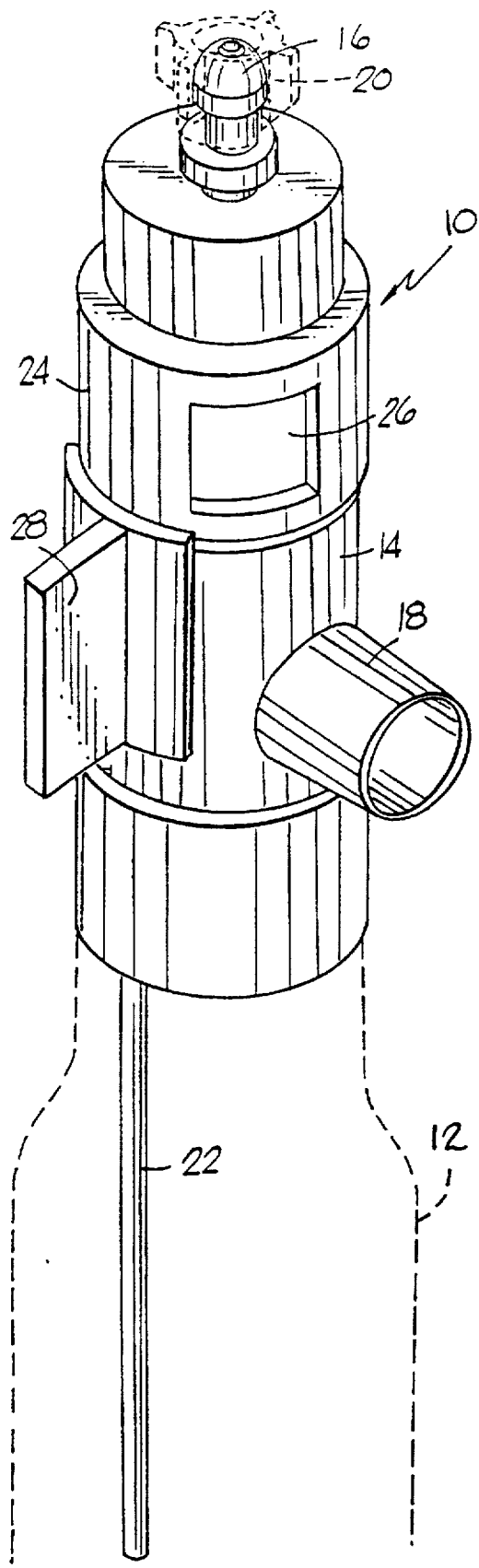
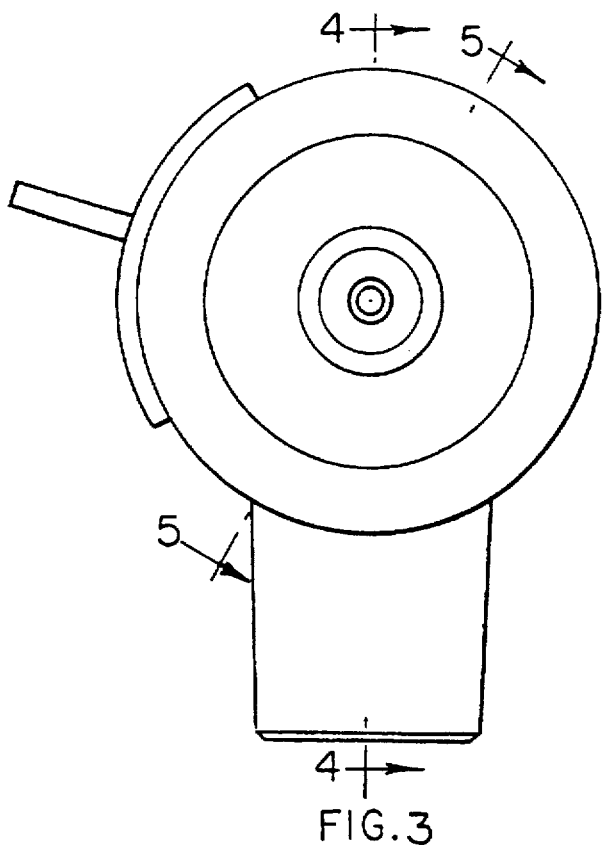
FIG.1
FIG.3

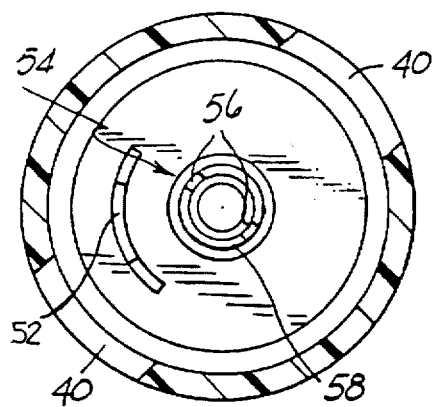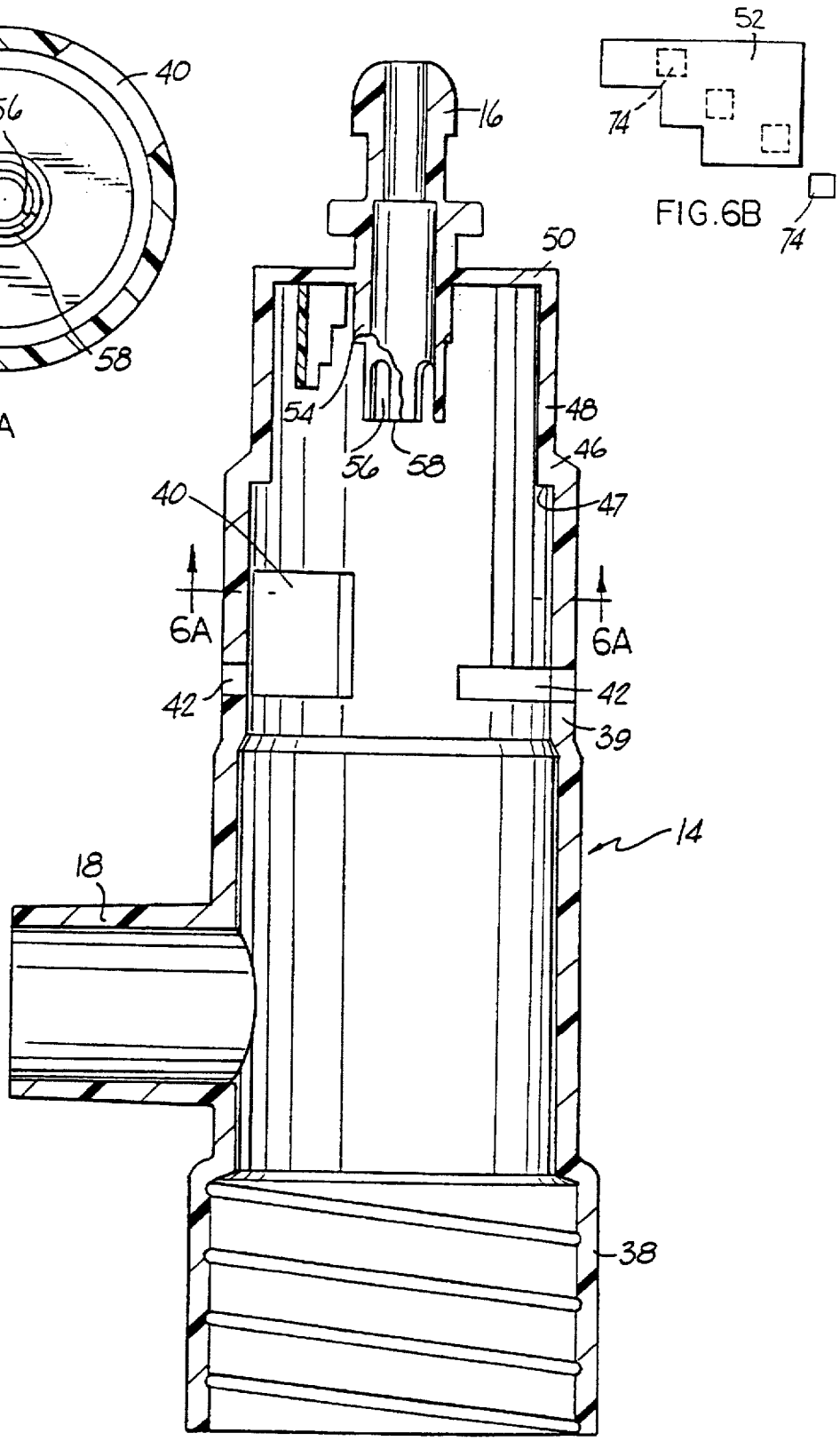
FIG. 6A
FIG. 6B
FIG. 6

VARIABLE OXYGEN CONCENTRATION HIGH-FLOW NEBULIZER

This application is a CIP of Ser. No. 08/524,278, filed Sep. 6, 1995 now abandoned.

BACKGROUND OF THE INVENTION

1. Technical Field

The present invention is directed toward a nebulizer, and more particularly toward a nebulizer with an adjustable range of oxygen concentration capable of maintaining high total gas flows.

2. Background Art

Nebulizers are used in medical applications for entraining a medical liquid or water into a high-velocity flow of a pressurized carrier gas such as oxygen for delivery of the entrained medical liquid or water in the form of a fine mist or aerosol to the lungs of a patient. In most therapeutic applications the carrier gas is oxygen. For simplicity, this specification will refer to the carrier gas as oxygen, but this is not intended as a limitation on the types of gasses which could be used as a carrier gas with the variable oxygen concentration high-flow nebulizer.

Michaels et al., U.S. Pat. No. 4,595,002 describes a nebulizer design which has enjoyed substantial commercial success. The nebulizer of Michaels has an oxygen nozzle which directs a high-velocity low pressure stream of oxygen in proximity to a conventional constriction venturi for drawing liquid from a reservoir through the constriction venturi to entrain the liquid from the venturi in the oxygen stream. The nebulized liquid and oxygen flow directly into a mixing chamber defined by a cylindrical housing. An opening or vent in the cylindrical housing permits ambient air to be drawn into the mixing chamber by the relatively low pressure, high velocity oxygen stream so as to dilute the concentration of the oxygen. Michaels further discloses a collar which surrounds the cylindrical body, the collar having a window which can be brought into or out of alignment with the vent in the housing by rotation of the collar relative to the housing so as to increase or decrease the effective opening of the vent. Michaels further teaches providing a scale on the collar which is graduated to reflect inspired oxygen concentrations which result from the window being opened a select amount. Thus, the nebulizer disclosed in Michaels provides a clinician a convenient and accurate control of oxygen concentration in a stream of respiratory gasses and nebulized liquid flowing to a patient.

The nebulizer described in Michaels is extremely effective at delivering oxygen/air mixtures containing less than 40% oxygen. At oxygen concentrations greater than 40%, the structure described in Michaels has been found to deliver total flow rates of respiratory gas (oxygen and ambient air) of less than 40 liters per minute. However, when a patient is in respiratory distress, the patient can often require 40 liters per minute or more of respiratory gasses. In order to provide the patient with a sufficient flow rate of respiratory gasses at high oxygen concentrations, clinicians have been required to use two or three nebulizers such as that described in Michaels connected in parallel.

Efforts have been made in the prior art to provide a single nebulizer which can provide a wide range of oxygen concentrations while providing a sufficient amount of respiratory gasses even at very high oxygen concentrations. Boiarski et al., U.S. Pat. No. 4,612,926, is one example in the prior art of an attempt to address this need. Boiarski teaches a nebulizer which is connectable to a standard 50 psig oxygen source for purportedly delivering nebulized air to a patient in oxygen concentrations of less than 30% to 100% while maintaining flow rates of at least 40 liters per minute for even relatively pure oxygen flows. Boiarski claims to accomplish this goal by providing a structure somewhat similar to that described above with respect to Michaels, only including a second valved oxygen nozzle that is not associated with a liquid supply venturi. The valve on the second nozzle in Boiarski allows a clinician to increase the rate of flow of oxygen as the amount of ambient air which can be aspirated is decreased by closing an ambient air vent.

The disclosure of Boiarski has several problems which prevents it from effectively addressing the need to provide a single nebulizer capable of providing a wide range of oxygen concentrations while at the same time providing a sufficient flow rate of respiratory gasses. Specifically, Boiarski does not provide liquid to the second nozzle for nebulization. Boiarski therefore requires a complex structure including a baffle which diverts oxygen from the second nozzle to prevent it from interfering with nebulization of liquid by oxygen exiting a first nozzle. This baffle also reduces the oxygen velocity significantly (from 300 m/s to 5 m/s) resulting in an increase in pressure above the air entrainment window which would make it difficult to have much control of total flow rates and oxygen percent at higher oxygen concentrations. Furthermore, Boiarski requires two separate adjustments (the air entrainment window and the second nozzle) to alter oxygen concentrations while maintaining adequate flow volumes, making Boiarski difficult for a clinician to use. Boiarski also fails to provide a clinician any way to determine the total flow rate of respiratory gasses to a patient so that the clinician can accurately adjust the second oxygen nozzle as the ambient air entrainment vents are opened or closed. In addition to making it difficult to use the Boiarski nebulizer, this deficiency in Boiarski creates the risk of the ambient air entrainment vents being inadvertently closed without a corresponding opening of the second valve which could deny a patient the necessary volume of respiratory gasses, leading to respiratory failure.

Medical Molding Corporation of America sells a MISTY OX nebulizer which attempts to tackle the problem of supplying a patient with sufficient air flow at a wide range of oxygen concentrations (21–100%). This MISTY OX requires connection to a separate compressed air source in addition to a standard 50 psig oxygen source. This requirement for a second pressurized gas supply makes the MISTY OX unsuitable for many clinical applications, particularly outside of an intensive care unit.

The present invention is intended to address one or more of the problems discussed above.

SUMMARY OF THE INVENTION

The present invention is directed toward a nebulizer for providing a variable percentage of inspired oxygen to a patient while maintaining a select minimum rate of flow of respiratory gasses and nebulized liquid to the patient. The nebulizer includes at least two oxygen nozzles, each oxygen nozzle having an inlet and outlet. A pressurized oxygen supply is connected in fluid communication with the inlet of each nozzle. A liquid outlet corresponding to each nozzle is positioned proximate the nozzle outlet of the corresponding nozzle for nebulization of liquid from the liquid outlet in a stream of oxygen flowing from the outlet of each nozzle. A liquid supply is connected in liquid communication with each liquid outlet. An oxygen adjustment valve is provided in fluid communication with at least one of the gas nozzles for selectively recruiting the at least one nozzle and preventing oxygen from flowing from the at least one nozzle.

The nebulizer may further include a liquid control mechanism operatively associated with the liquid supply for selectively allowing and preventing flow of liquid through a select liquid outlet. In a preferred form the nebulizer includes a coordinator operatively associated between the liquid control and the oxygen adjustment valve for causing the liquid control to prevent flow of liquid through a liquid outlet when the oxygen adjustment valve selectively prevents gas from flowing from a corresponding nozzle and for causing the liquid control to allow flow of liquid through the liquid outlet when the oxygen adjustment valve selectively recruits the nozzle.

The nebulizer may further include a housing having a wall and a mixing chamber therein for receiving oxygen and nebulized liquid from the oxygen nozzle outlets and corresponding liquid outlets. The wall has at least one ambient air vent for providing a flow of ambient air into the mixing chamber and an outlet for exhausting the nebulized liquid, gas and ambient air. A vent controller is provided in operative association with the ambient air vent for selectively varying the effective size of the ambient air vent between fully open and fully closed. Preferably a linking structure is provided between the oxygen adjustment valve and the vent controller so that as the vent controller decreases the effective size of the vent beyond a select amount, the oxygen adjustment valve automatically increases the number of recruited nozzles and as the vent controller is adjusted to increase the effective size of the vent, the oxygen adjustment valve automatically decreases the number of recruited nozzles.

The oxygen adjustment valve may comprise a cylinder having first and second ends and a hole through the cylinder wall corresponding to each oxygen nozzle, each hole being spaced lengthwise along the cylinder wall between the first and second ends. A conduit connects each hole to the corresponding nozzle inlet. A plunger having a cylindrical side wall with an open end corresponding to the first end of the cylinder and a closed end defining a fluid plenum within the plunger is disposed in the cylinder. The outer diameter of the plunger is less than the inner diameter of the cylinder to define an annular space therebetween. The plunger includes an orifice in the sidewall between the fluid plenum and outside the fluid plenum and a radial seal between its closed end and the orifice forming a fluid tight seal between the interior of the cylinder and the side wall of the plunger. A pressurized gas source is in fluid communication with the open end of the plunger. An adjuster is provided for moving the plunger lengthwise within the cylinder in a first direction to recruit select nozzles by moving the seal between the hole corresponding to the nozzle and the second end of the cylinder and in a second direction to prevent flow to select nozzles by moving the seal between the corresponding hole and the first end of the cylinder.

A second embodiment of the nebulizer for providing a select rate of flow of gas entraining a liquid includes a cylindrical housing having a closed end and a gas connecting structure on the closed end for connecting a pressurized gas supply in communication with the cylindrical housing interior. A primary nozzle disk having at least two gas nozzles is positioned proximate but spaced from the closed end of the cylindrical housing. A valve disk having an outer diameter no greater than the inner diameter of the housing is positioned between the primary nozzle disk and the closed end of the cylindrical housing with integral valves on the valve disk in operative association with at least one of the two gas nozzles. The valves on the valve disk are actuatable between a recruited and a closed position for selectively recruiting and closing a corresponding gas nozzle. An actuator on the cylinder is operatively associated with each valve for actuating each valve between a recruited and a closed position by relative rotation between the valve disk and the housing. A liquid outlet corresponding to each gas nozzle is positioned proximate the gas outlet of the corresponding nozzle for nebulization of liquid from the liquid outlet in a stream of carrier gas flowing from the gas outlet of each nozzle. A liquid supply is connected in liquid communication with the liquid outlet.

The second embodiment may further include a secondary nozzle disk having a top and a bottom, the secondary nozzle disk having a hole therethrough forming each of the liquid outlets. A slot is provided in the top of the secondary nozzle disk corresponding to each liquid outlet and extends between a common liquid supply hole and each outlet. The secondary nozzle disk top abuts a bottom surface of the primary nozzle disk in fluid tight relation whereby the slots form fluid tight disk conduits. A liquid supply tube extends between the common liquid supply hole and a liquid supply to provide liquid to each of the liquid outlets by virtue of a negative pressure created by a flow of pressurized gas through the gas nozzles.

The nebulizer described herein allows for variation of the percentage of carrier gas (typically oxygen) between 28-100% while maintaining the total rate of flow of respiratory gasses emanating from the nebulizer at least 40 liters per minute. The nebulizer also provides for automatic variation in the number of recruited oxygen nozzles as the ambient air vent is opened or closed so as to automatically assure a select rate of flow of respiratory gasses as the oxygen concentration is varied by one simple operation. The nebulizer provides these significant advantages over prior art nebulizers without requiring a compressed oxygen source apart from a standard 50 psig oxygen connection typically found in hospital and other clinical settings. This feature facilitates use of the nebulizer outside of the intensive care unit in most hospitals, and in sub-acute hospitals and home care applications. The versatility of the nebulizer allows hospitals and other care providers to stock only this single nebulizer to provide a wide range of carrier gas concentrations while maintaining necessary respiratory gas flow rates. Moreover, the nebulizer operates through simple mechanical connections and can be made from relatively few inexpensive injection molded parts, resulting in a nebulizer that is inexpensive to manufacture, yet highly accurate and easy to operate.

BRIEF DESCRIPTION OF THE DRAWINGS

FIG. 1 is a perspective view of a first embodiment of a variable oxygen concentration high-flow nebulizer of the present invention attached to a medication bottle;

FIG. 3 is a plan view of the nebulizer of FIG. 1;

FIG. 6 is a cross-sectional view of the nebulizer housing;

FIG. 6A is a cross-sectional view taken along line 6A—6A of FIG. 6;

FIG. 6B is an elevational view of the stepped entrainment shield depicted in FIG. 6 with the liquid entrainment windows indicated in phantom lines;

DETAILED DESCRIPTION OF THE PREFERRED EMBODIMENTS

Figure 2A:
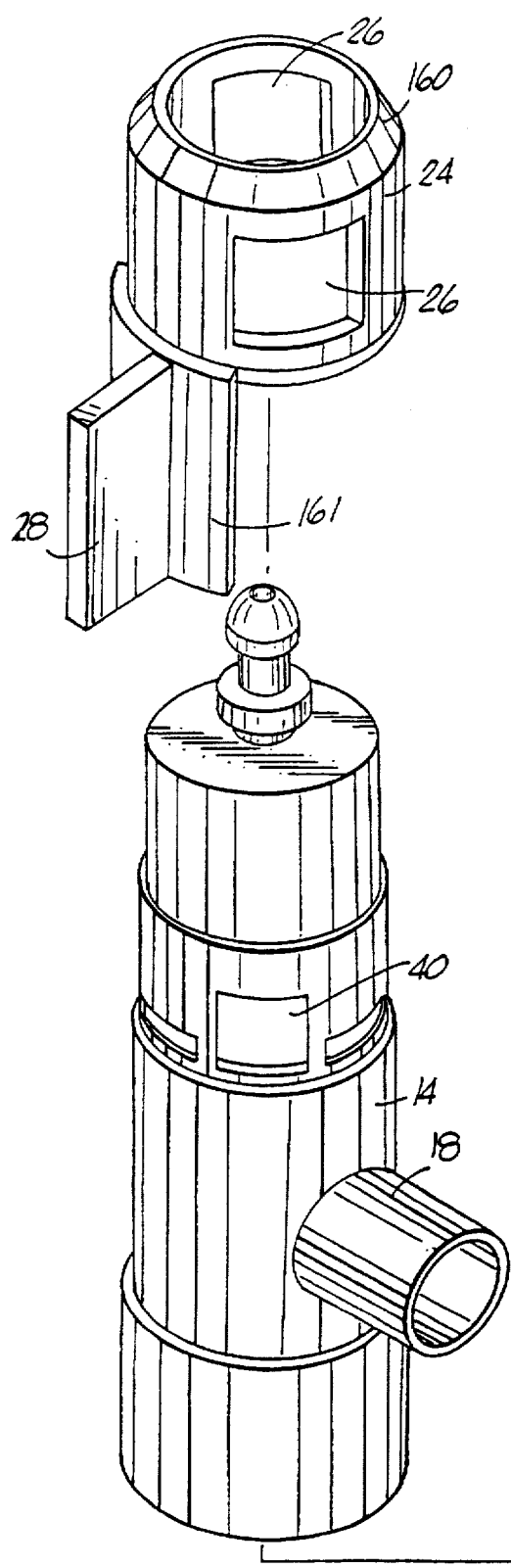
FIG. 2 is an exploded view of the nebulizer of FIG. 1.

A first embodiment of the variable oxygen concentration high-flow nebulizer 10 of the present invention is shown threadably engaged to a fluid reservoir or medication bottle 12 in FIG. 1. Elements of the nebulizer 10 which are clearly seen in FIG. 1 include a cylindrical nebulizer housing 14 having a pressurized gas inlet 16 and an outlet 18. A conventional screw cap 20 is shown in phantom lines attached to the pressurized gas inlet 16. Descending from the bottom of the nebulizer housing 14 and into the bottle 12 is a dip tube 22. Enveloping a portion of the nebulizer housing 14 is a flow control collar 24 having an ambient air window 26 and an adjustment lever 28.

In operation, the pressurized gas inlet 16 is connected to a pressurized carrier gas supply (not shown), typically oxygen at a pressure which is generally at or about 50 psig. by attaching a conduit (not shown) from the pressurized gas source to the pressurized gas inlet 16 and securing a fitting on the pressurized gas conduit to the pressurized gas inlet 16 by means of the screw cap 20. The nebulizer housing 14 is threadably attached to a liquid supply bottle 12 with a distal end of the dip tube 22 within liquid carried by the bottle. Upon flow of pressurized gas into the inlet 16, liquid from the bottle 12 is drawn into the nebulizer through the dip tube 22, entrained in the carrier gas and mixed with any air entering the ambient air window 26. A resulting mixture of the air, carrier gas and nebulized liquid exits the outlet 18 which is in turn connected to a patient through a respiratory support system (not shown). The detailed operation of the nebulizer 10 and the interaction of its components will be discussed in greater detail below.

Figure 2A:
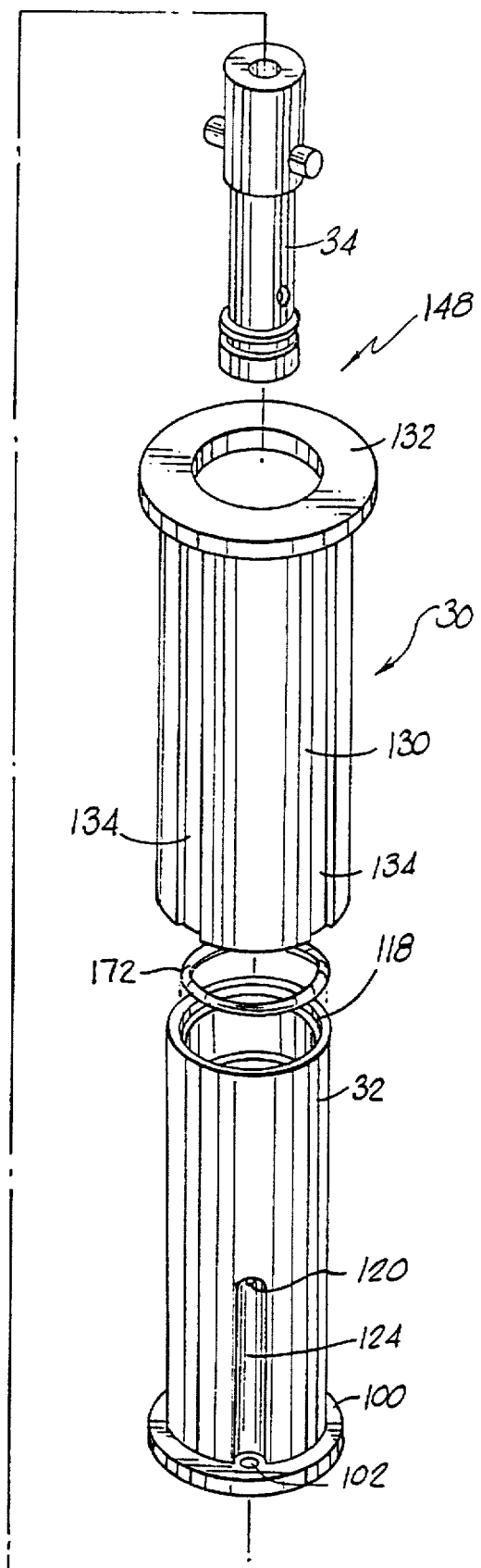
Figure 2B:
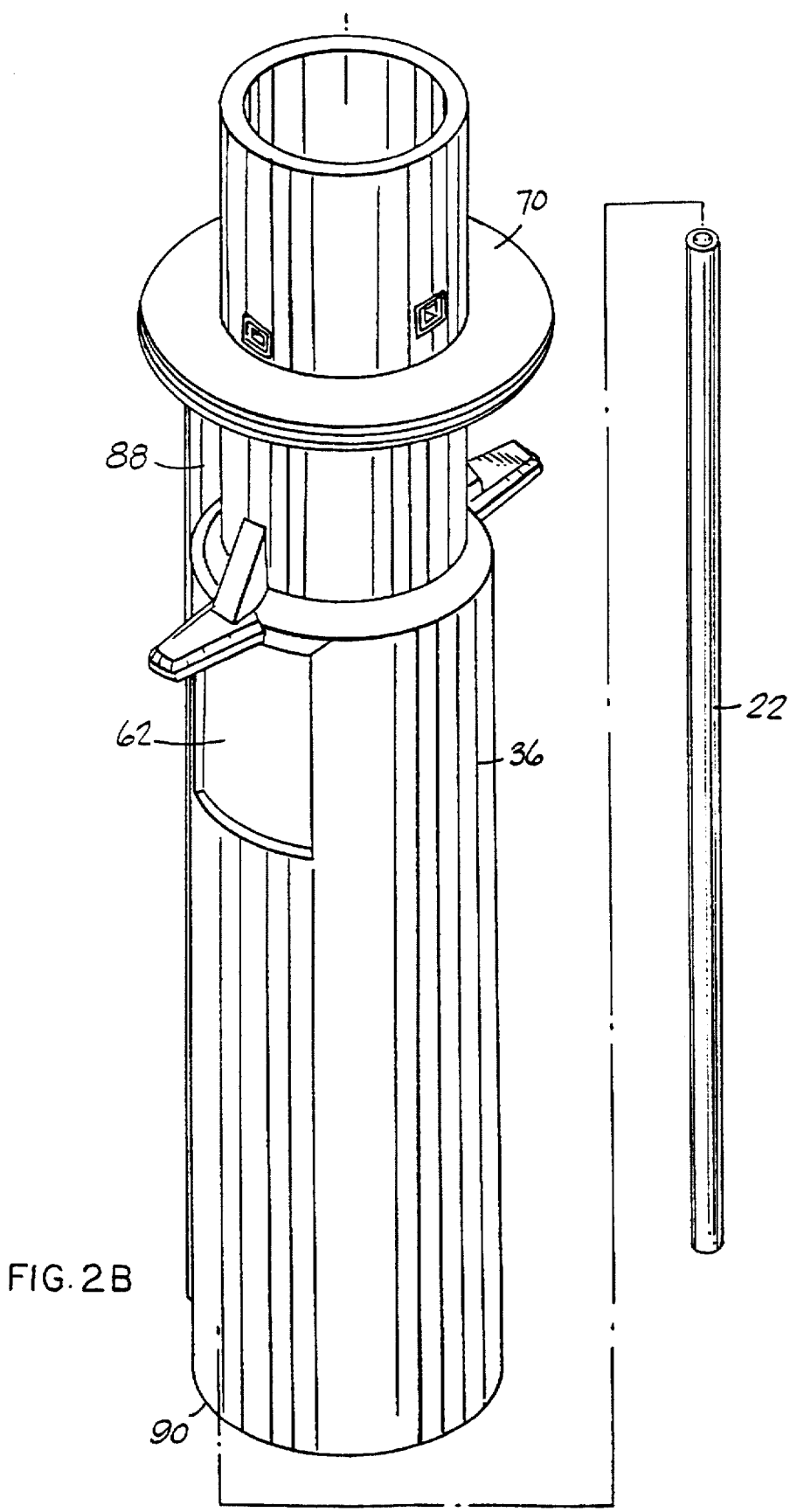

FIG. 2 is an exploded view of the first embodiment of the nebulizer 10 illustrating its components and the relative positions of the components during assembly. The flow control collar 24 fits over the top of the housing 14, enveloping a portion of the housing 14. The components inside the housing 14 include an outer cylinder 30 which receives an oxygen control cylinder 32 which in turn receives a plunger 34. The outer cylinder 30, oxygen control cylinder 32 and plunger 34, once assembled, are received in the top of the interior frame 36. An end of the dip tube 22 is received in a female receptacle at the bottom of the interior frame 36. The interior frame 36 is then received in the bottom of the housing 14. The various components are shown assembled and in cross-section in FIGS. 4 and 5 which are described in greater detail below.

The cylindrical nebulizer housing 14 is shown in cross-section in FIGS. 6, 6A and 6B. In addition to the pressurized gas inlet 16 and the outlet 18 described above, the cylindrical nebulizer housing 14 includes an internally threaded base 38 for threaded engagement to an external thread (not shown) on the top of the bottle 12. Above the base 38 is a central portion 39 of the housing 14. The outlet 18 is located in the central portion 39. Above the outlet 18 are a pair of air entrainment vents 40 through the side wall of the nebulizer housing 180° apart from each other. Only one air entrainment vent 40 is shown in FIG. 6, although both can be viewed in FIG. 6A. Between the air entrainment vents 40 are arcuate slots 42 through the side wall on opposite sides of the housing 14. Each of the arcuate slots 42 extend through an arc of approximately 100° through the wall of the nebulizer housing 14. An annular inclined shoulder 46 joins a top portion 48 and the central portion 39 of the nebulizer housing 14. Descending from the top 50 of the nebulizer housing 14 within the top portion 48 is an arcuate stepped entrainment shield 52. The stepped entrainment shield 52 is shown in greater detail in FIG. 6B and will be discussed further below. Also extending downward from the top 50 of the housing 14 about the longitudinal axis of the housing 14 is a plunger control cylinder 54 having a pair of 180° spaced elongate slots 56 extending axially upward from its bottom edge 58. FIG. 6A is a cross-sectional view of FIG. 6 illustrating the air entrainment vents 40, the arcuate stepped liquid entrainment shield 52 and the plunger control cylinder 54.

Figure 8:
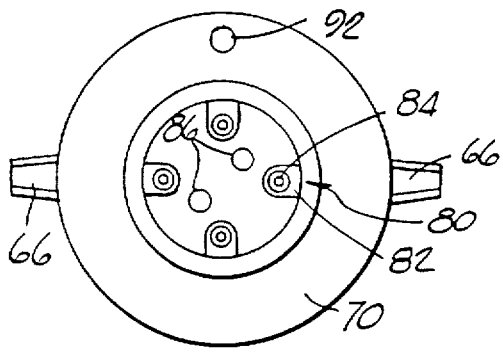
FIG. 8 is a bottom view of the interior frame of the nebulizer depicted in FIG. 7.
Figure 7:
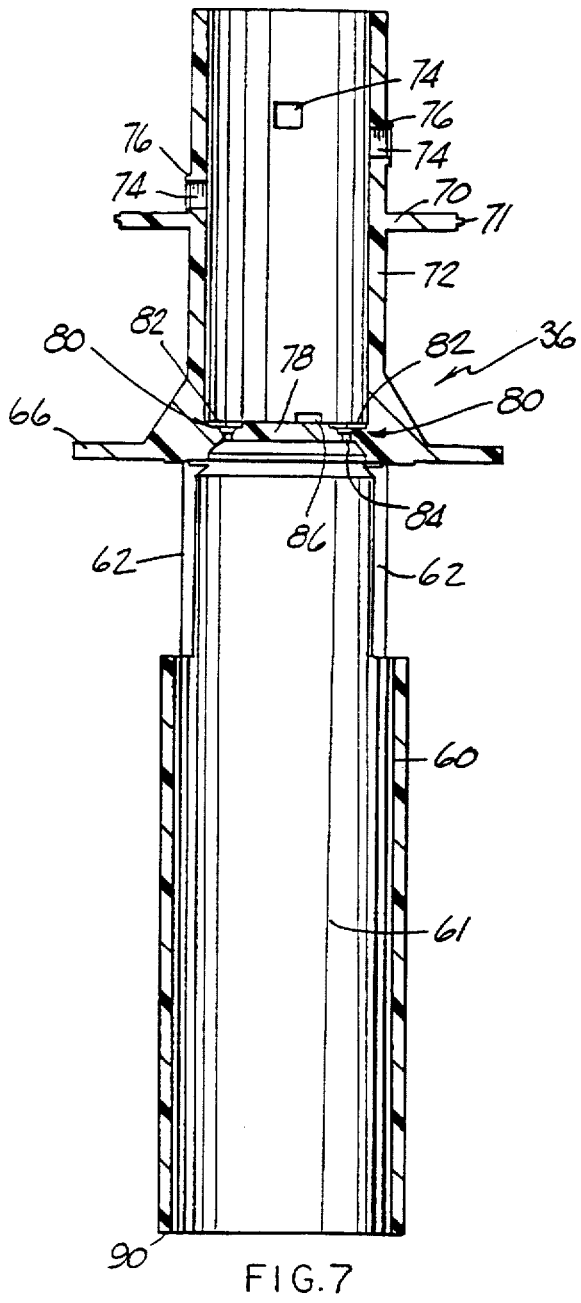
FIG. 7 is a cross-sectional view of the interior frame of the nebulizer depicted in FIG. 2.
Figure 12:
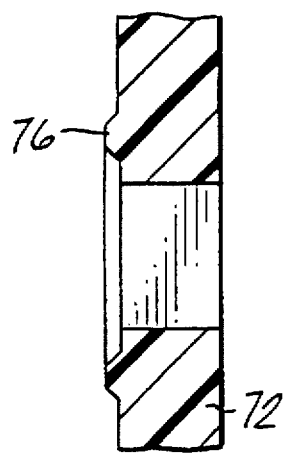
FIG. 12 is an enlarged cross-sectional view of a liquid entrainment window on the interior frame depicted in FIG. 7.
Figure 13:
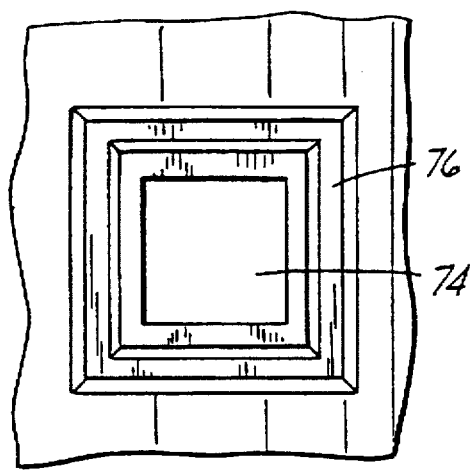
FIG. 13 is an elevational view of the liquid entrainment window of FIG. 12.
Figure 14:
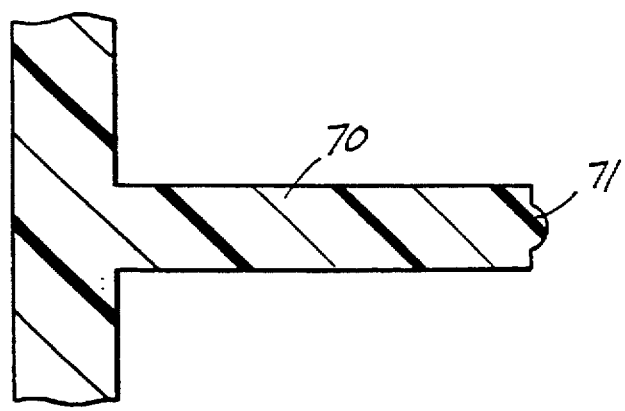
FIG. 14 is an enlarged view of a cross-section of the annular partition depicted in FIG. 7.

The interior frame 36 is described with reference to FIGS. 7, 8 and 2. The interior frame 36 is generally cylindrical. It includes a bottom portion 60 of generally a uniform diameter having a pair of mixing air access ports 62 spaced circumferentially 180° apart. Above the mixing air access ports 62 a pair of connecting arms 66 extend in opposite directions away from the cylindrical side wall of the interior frame 36. Above the connecting arms 66 is an annular partition 70 which extends radially outward from a uniform inner diameter upper portion 72 of the interior frame 36. At the distal edge of the annular partition 70 is a semi-circular protrusion 71. shown in greater detail in FIG. 14. Spaced axially and at 90° intervals radially above the annular partition 70 are four liquid access windows 74. As best seen in FIGS. 12 and 13. a ridge 76 extends outwardly from the uniform diameter portion 72 and frames each of the liquid access windows 74. Preferably the ridges protrude about 0.002–0.005 inch. In the particular embodiment illustrated herein the liquid access windows 74 and the ridges 76 are square; however, the liquid access windows 74 and the ridges 76 could have any shape, including circular.

Inside an interior frame 36 between the uniform diameter lower portion 60 and the uniform diameter upper portion 72 is an orifice plate 78. The orifice plate 78 has four liquid delivery outlets 80, as best viewed in FIG. 8. Each liquid delivery outlet 80 includes a feeder channel 82 in fluid communication with a liquid or secondary nozzle 84. On the top surface of the orifice plate 78 are a pair of keying protrusions 86.

Referring to FIG. 2. a fin 88 extends from the interior frame 36 and runs between the bottom of the annular partition 70 and the bottom edge 90 of the frame member. A conduit (not shown) is formed within the fin 88 and runs the length of the fin 88 between a liquid supply hole 92 in the annular partition 70 (see FIG. 8) and a hole (not shown) in the bottom edge of the fin 88. The dip tube 22 is configured to fit in the hole in the bottom edge of the fin 88 as indicated in FIG. 2.

Figure 9:
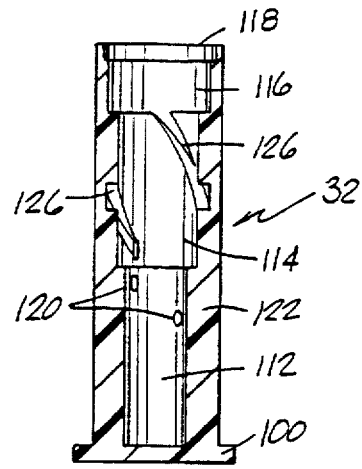
FIG. 9 is a cross-sectional view of the oxygen control cylinder depicted in FIG. 2.
Figure 11:
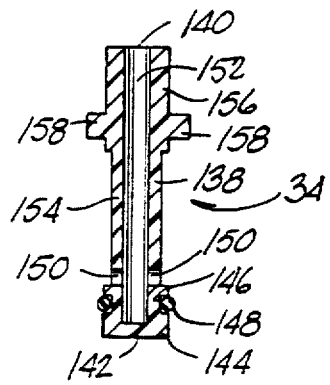
FIG. 11 is a cross-sectional view of the plunger depicted in FIG. 2.

The oxygen control cylinder 32 is shown in cross section in FIG. 9. The oxygen control cylinder 32 has an annular flange 100 around a bottom edge. Extending through the annular flange are a first primary nozzle 102, a second primary nozzle 104, third primary nozzle 106 and a fourth primary nozzle 108. Below the operation of the nebulizer 10 will be discussed in greater detail. For now, the reader must understand that the nebulizer recruits nozzles 104, 106, 108 as the entrainment vents 40 are closed. The orifice of each of the four primary nozzles is sized to provide the necessary oxygen flow rate as the air entrainment vents 40 are closed. The diameter of the first primary nozzle 102 is about 0.017", the diameter of the second primary nozzle 104 is about 0.025", the diameter of the third primary nozzle 106 is about 0.034" and the diameter of the fourth primary nozzle 108 is about 0.042". The nozzles increase in size because as the ambient air vents are closed the size of each additionally recruited nozzle must increase in diameter in order to provide adequate flow. As illustrated in FIG. 9. within the bottom surface of the oxygen control cylinder 32 are a pair of keying depressions 110 spaced to received the keying protrusions 86 of the interior frame 36.

The interior of the oxygen control cylinder 32 includes first 112, second 114, third 116 and fourth 118 cylindrical sections of increasing diameter and decreasing axial length, each cylindrical section being separated by an annular shoulder. Four oxygen flow holes 120 (two shown in FIG. 9) extend through the cylindrical side wall 138 of the oxygen control cylinder 32 and are spaced at 90° intervals radially and spaced axially along the length of the first interior chamber 112. Each of the holes 120 terminates at the outer surface of the cylindrical side wall at the top end of an oxygen supply groove 124 (see FIG. 2). At the bottom of each air supply groove 124 is one of the primary nozzles 102, 104, 106, 108. Formed in the wall of the second interior chamber 114 are a pair of threading grooves 126.

Figure 4:
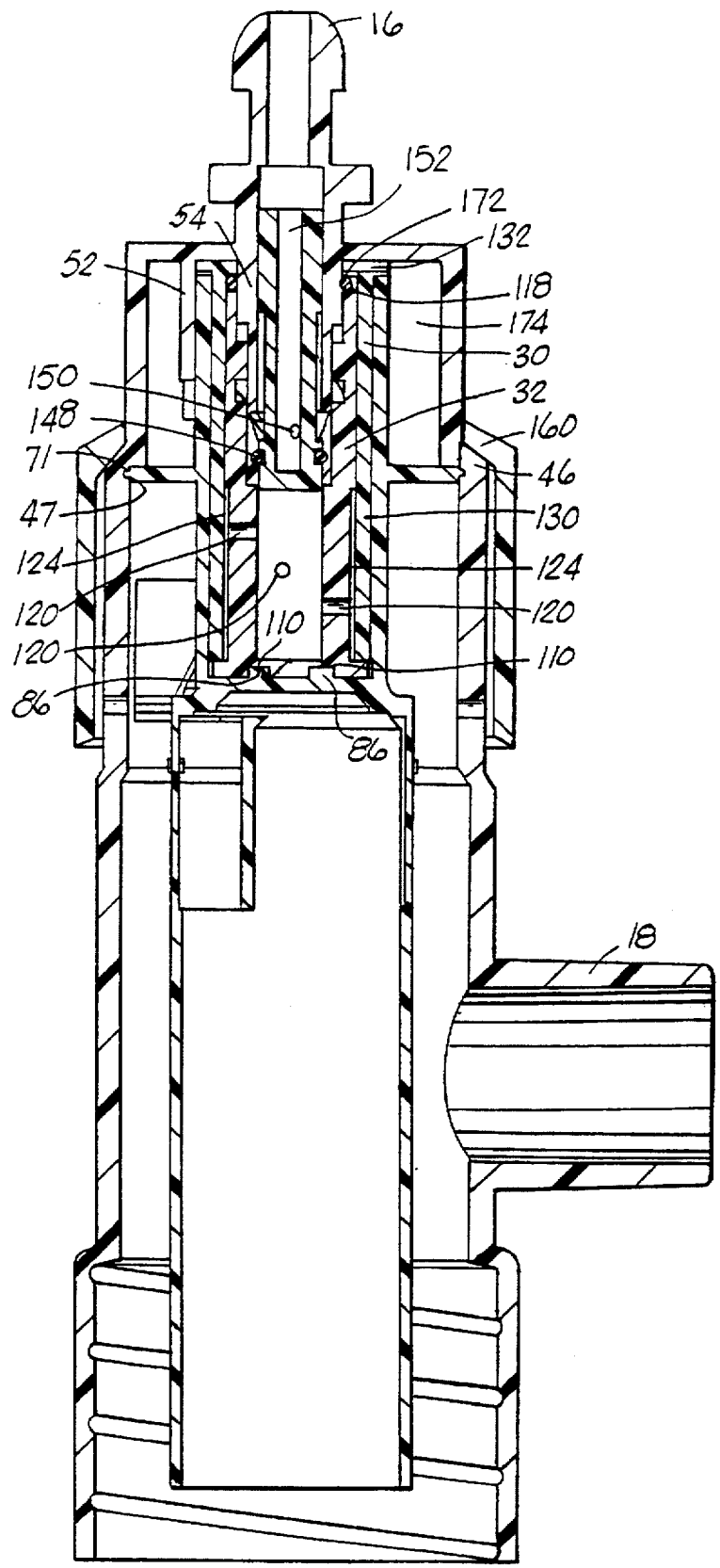
FIG. 4 is a cross-sectional view of the nebulizer of FIG. 1 taken along line 4—4 of FIG. 3.

The outer cylinder 30 is illustrated in FIG. 2 and has a cylindrical side wall 130 with an annular T-flange 132 at its upper edge (see FIG. 4). Radially spaced at 90° intervals and extending axially lengthwise from the bottom of the annular T-flange 132 are four liquid supply grooves 134 (only two shown in FIG. 2).

Figure 10:
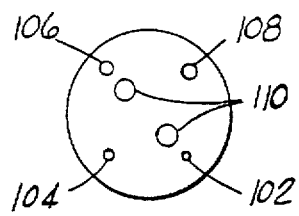
FIG. 10 is a bottom view of the oxygen control cylinder of FIG. 8.

The plunger 34 is shown in cross section in FIG. 10. The plunger 34 has a cylindrical side wall 138 with an open top 140 and a closed bottom 142. The cylindrical side wall 138 has a leading portion 144 with an annular O-ring groove 146 receiving a plunger O-ring 148. Immediately above the leading portion 144 are a pair of 180° spaced oxygen orifices 150 which extend between a plenum 152 within the cylindrical side wall 138 and the exterior of the plunger 34. The oxygen orifices 150 reside in a reduced diameter central portion 154 of the cylindrical side wall 138. A trailing portion 156 of the cylindrical side wall 138 is about equal in diameter to the leading portion 144. A pair of thread engaging studs 158 extend radially from the trailing portion 156 and are spaced 180° from each other.

The flow control collar 24 is best viewed in FIG. 2. It includes a pair of 180° spaced ambient air windows 26 of about the same dimensions as the air entrainment vents 40 of the nebulizer housing 14. At the top of the flow control collar is an inclined upper shoulder 160 which defines a circular open top of the flow control collar 24. The control lever 28 extends lengthwise along a bottom shield 161 of the flow control collar 24.

Figure 5:
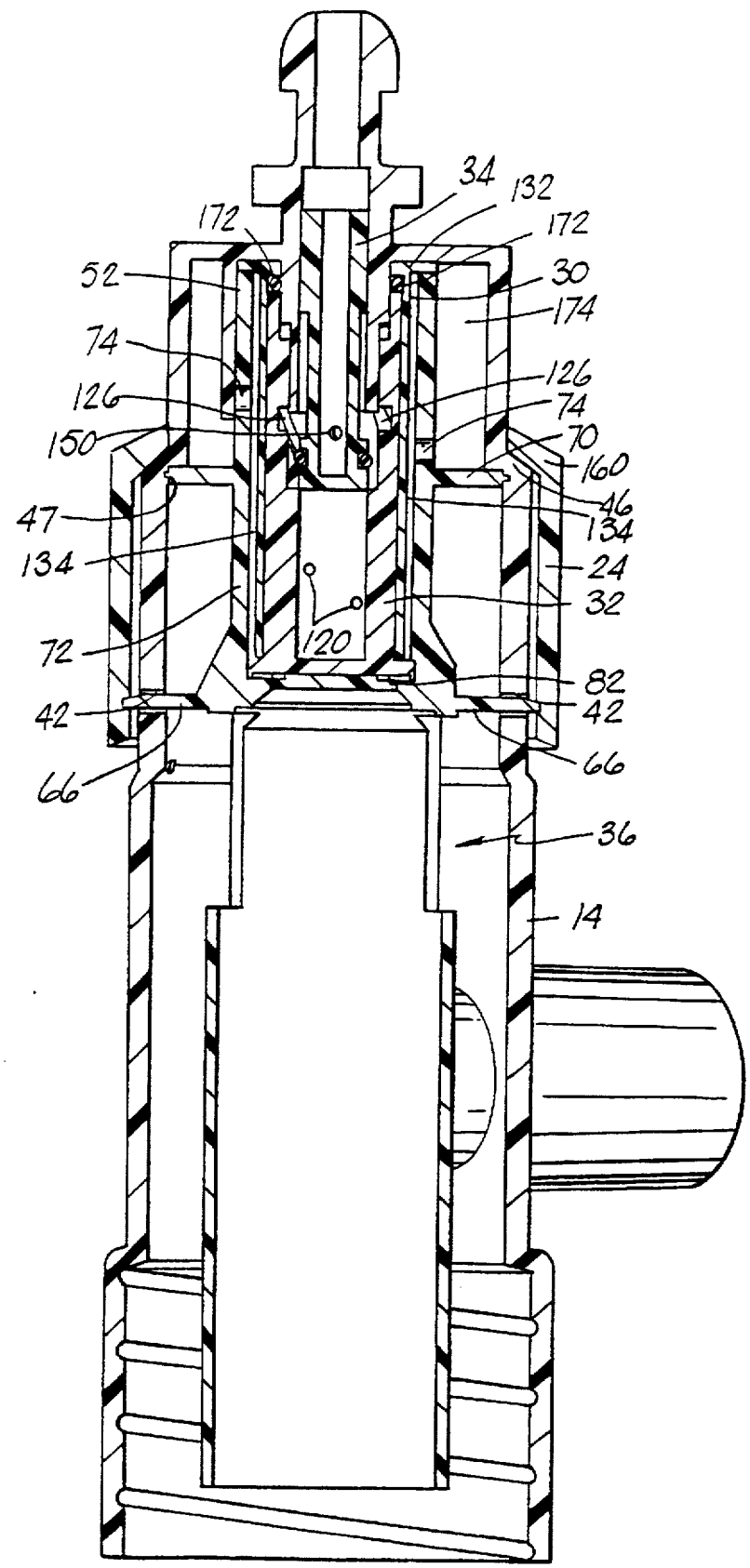
FIG. 5 is a cross-sectional view of the nebulizer of FIG. 1 taken along line 5—5 of FIG. 3.

The variable oxygen concentration high-flow nebulizer 10 is shown fully assembled (excluding only the screw cap 20) in FIGS. 5 and 6 which are cross-sectional views taken along the corresponding lines indicated in FIG. 3. The plunger 34 resides primarily within the interior of the oxygen control cylinder 32. Although not visible in FIGS. 4 and 5, the thread engaging studs 158 of the plunger 34 are received within the threading grooves 126 of the oxygen control cylinder 32. The outer cylinder 30 fits over the oxygen control cylinder 32 with an O-ring 172 being captured between the fourth interior chamber 118, the underside of the inwardly extending portion of the T-flange 132 of the outer cylinder 30 and the flow control cylinder 54. When the nebulizer 10 is fully assembled, the O-ring 172 prevents high pressure oxygen from escaping into the liquid aspiration chamber 174. The plunger 34, oxygen control cylinder 32 and outer cylinder 30 are received within the interior of the uniform diameter upper portion 72 of the interior frame 36. The keying depressions 110 in the bottom of the oxygen control cylinder 32 are aligned with and receive the keying protrusions 86 extending from the upper surface of the orifice plate 78 within the interior frame 36 (see FIG. 4). The interior frame 36 is inserted within the bottom of the cylindrical nebulizer housing 14 and aligned so that the thread engaging studs 158 of the plunger 34 are received within the elongate slots 56 in the plunger control cylinder 54. In addition, referring to FIG. 5, the connecting arms 66 of the interior frame 36 fit into and extend through arcuate slots 42 in the cylindrical side wall of the cylindrical nebulizer housing 14. The connecting arms 66 are integrally injection molded with the interior frame 36 and are sufficiently flexible that as the interior frame 36 is slid into the nebulizer housing 14 the arms 66 snap outward through the slits 42. The annular partition 70 abuts the inner shoulder 47 in the interior of the nebulizer housing 14. As best seen in FIG. 4, the arcuate circumferencial ridge 71 (which extends about 0.002–0.005 inch) engages the interior of the housing 14 at the inner shoulder 47 forming a liquid-tight seal therewith and defining an annular liquid aspiration chamber 174 between the interior frame 36 and the interior of the nebulizer housing 14. The arcuate stepped liquid entrainment shield 52 covers a portion of the exterior of the top of the interior frame 36, as seen in FIGS. 4 and 5 and, as seen in FIG. 5, depending upon the relative orientation between the nebulizer housing 14 and the interior frame 36, can cover one or more of the liquid entrainment windows 74. This relationship will be discussed in greater detail below with respect to the operation of the nebulizer. The ridges 76, (see FIGS. 12 and 13) protrude sufficiently from the interior frame 36 (0.002–0.005 inch) to provide an adequate seal with the interior surface of the arcuate stepped liquid entrainment shield 52.

As seen in FIGS. 4 and 5, the inclined shoulder 160 of the flow control collar 24 rests upon the annular inclined shoulder 46 of the nebulizer housing 14. The connecting arms 66 which extend through the arcuate slots 42, 44 in the side wall of the nebulizer housing 14 engage the interior of the collar 24, as seen in FIG. 5. The ambient air windows 26 are brought into and out of alignment with the air entrainment vents 40 of the nebulizer housing 14 by rotation of the collar 24 to control ambient air mixing as discussed in further detail below.

Figure 15:
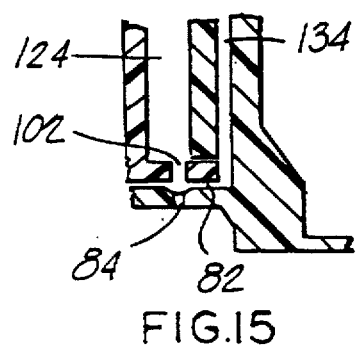
FIG. 15 is a cross-sectional view illustrating alignment of the primary and secondary nozzles.

With the nebulizer components assembled as discussed above, as seen in FIG. 5, the liquid supply grooves 134 of the outer cylinder 30 in cooperation with the inner wall of the uniform diameter upper portion 72 of the interior frame 36 define liquid supply conduits between the liquid access windows 74 and the secondary nozzles 82. Referring to FIG. 4, the air supply grooves 124 of the oxygen control cylinder 32 cooperate with the interior surface of the cylindrical side wall 130 of the outer cylinder 30 to define oxygen supply conduits to deliver oxygen between the oxygen holes 120 and the primary nozzles, 102, 104, 106, 108. FIG. 15 illustrates the first primary nozzle 102 aligned with a liquid or secondary nozzle 84. Each of the other primary nozzles 104, 106, 108 are similarly aligned with a liquid nozzle 84. Referring to FIG. 4, pressurized oxygen flows through the inlet 16 into the plunger plenum 152, out of the oxygen orifice 150, though an oxygen flow hole 120, through a corresponding oxygen supply conduit and out the first primary nozzle 102. Referring to FIGS. 5 and 15, the high velocity of the oxygen at the primary nozzle 102 creates a negative pressure at the secondary nozzle outlet 84 which draws liquid up the dip tube 22, though a liquid supply hole 92 in the annular partition 70 (see FIG. 8), into the liquid aspiration chamber 174, though a liquid entrainment window 74, through a corresponding liquid supply conduit 134, through the feeder channel 82 to the secondary nozzle 84 where the high velocity oxygen nebulizes the liquid.

The first primary nozzle 102 is always open as is the corresponding liquid entrainment window 74 so at least this one nozzle pair is nebulizing liquid. FIGS. 4 and 5 illustrate the nebulizer 10 with only the primary nozzle 102 and corresponding liquid entrainment window 74 recruited. In this mode the plunger 34 is withdrawn from the first interior chamber of the oxygen control cylinder 32 so that the plunger O-ring 148 resides above all but the one oxygen hole 120 corresponding to the primary nozzle 102. At the same time, the arcuate stepped liquid entrainment shield 52 covers each of the liquid entrainment windows 74 except the one associated with the secondary nozzle corresponding to the primary nozzle 102 (see FIG. 6B). Also, in this mode the air entrainment vents 40 are fully aligned with the ambient air windows 26 so that a maximum amount of ambient air is available for mixing with the carrier gas and nebulized liquid as it exits the recruited nozzle pair. Ambient air is drawn into the mixing or access ports 62 by negative pressure created by the high velocity oxygen exiting the primary nozzle 102 and the ambient air, oxygen and nebulized liquid are mixed in the mixing chamber 61 in the uniform diameter lower portion 60 of the interior frame 36. The mixture of gasses and liquids then flows out of the bottom of the mixing chamber 61 and out the outlet 18 for delivery to a patient.

Figure 17:
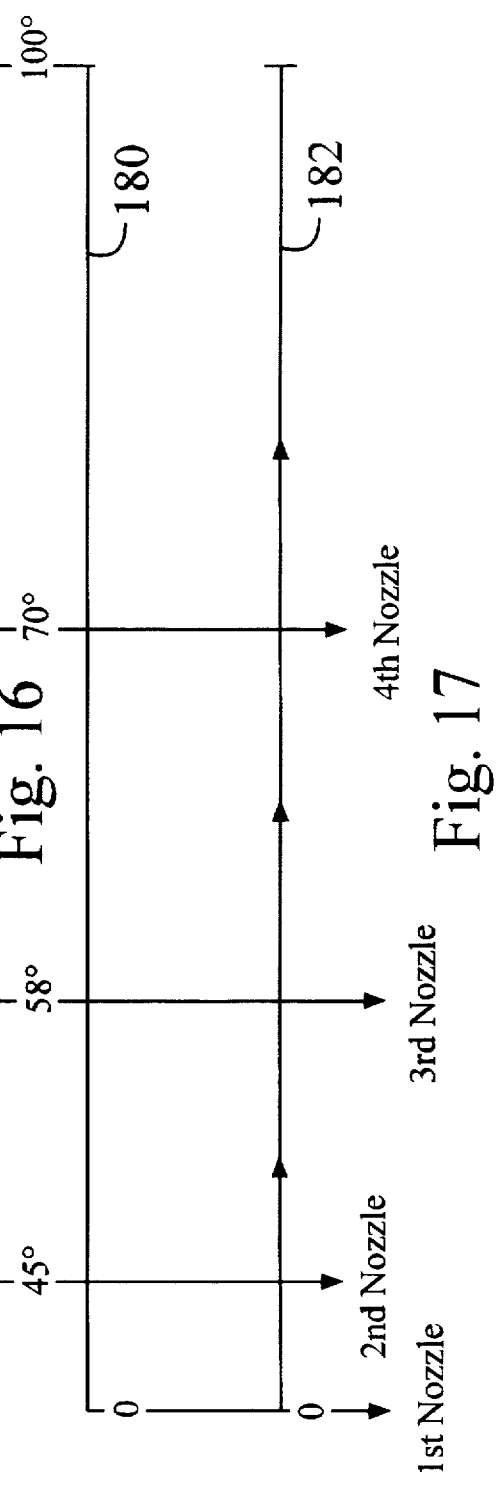
FIG. 17 is a chart illustrating the degree of rotation of the control collar at which the oxygen nozzles are recruited.

Should a clinician desire to increase the percentage of oxygen supplied to a patient, the collar 24 is rotated clockwise relative to the nebulizer housing 14. As the collar is rotated the ambient air windows 26 are brought out of full alignment with the air entrainment vents 40, decreasing the effective opening for ambient air to enter the mixing chamber. Because the connecting arms 66 of the interior frame 36 are fixedly connected to the flow control collar 24 and the oxygen control cylinder 32 is attached by a keyed connection to the orifice plate 78 of the interior frame 36, the oxygen control cylinder 32 is caused to rotate with the collar 24. The elongate slots 56 which receive the thread engaging studs 158 prevent the plunger 34 from turning with the oxygen control cylinder 32. However, because the thread engaging studs 158 threadably engage the threading grooves 126 on the interior of the oxygen control cylinder 32, the plunger 34 is driven downward as viewed in FIGS. 4 and 5 or further into the oxygen control cylinder 32. Once the collar has been turned sufficiently so that the plunger O-ring 148 resides between the next carrier gas hole 122 and the bottom of the oxygen control cylinder 32 (approximately 45° as seen in FIG. 17), carrier gas is then able to enter the next hole 122 and flow to the second primary nozzle 104 through the corresponding carrier gas supply groove 124. Simultaneously, as air is allowed to flow to the next carrier gas hole 122, the outer cylinder 30 is rotated relative to the arcuate stepped liquid entrainment shield 52 affixed to the top 50 of the nebulizer housing 14 causing the corresponding liquid access window 74 to become uncovered. Thus, liquid is able to flow from the liquid aspiration chamber 174 through the liquid access window 74 and through the corresponding liquid supply groove 134 through the feeder channel and to the corresponding secondary nozzle 84. As a result, two nozzles are now recruited and the ambient air windows 26 have moved out of full alignment with the air entrainment vents 40, therefore closing the air entrainment vents 40 providing a higher concentration of oxygen, while increasing the flow of oxygen so as to maintain an acceptable total flow rate of respiratory gasses to the patient. In a like manner, further rotation of the collar clockwise relative to the nebulizer housing 14 closes the air entrainment vents 40 further while simultaneously recruiting additional nozzle pairs by downward movement of the plunger 30 and simultaneous rotation of the arcuate stepped liquid entrainment shield 52 until the air entrainment vents 40 are fully closed and all four nozzles are recruited and involved in nebulizing liquid for supply to the patient. Turning of the collar counter-clockwise relative to the housing will stop the flow of liquid and air to the various nozzles as the plunger 34 is caused to move upward within the oxygen control cylinder 32 and as the arcuate stepped liquid entrainment shield 52 simultaneously seals corresponding liquid access windows, while the ambient air windows 26 align with the air entrainment vents 40 to admit more air. However, even with the plunger at its most withdrawn state from the inner cylinder, one liquid and air nozzle pair will remain recruited.

The top portion 48 of the nebulizer housing 14 is shaped to be received within a toroidal shaped heater (not shown) for heating liquid residing within the liquid aspiration chamber 174. As is well known in the art, the use of such a heater will increase the liquid temperature, thereby increasing the humidity content for the delivery of aerosol to a patient.

Figure 18:
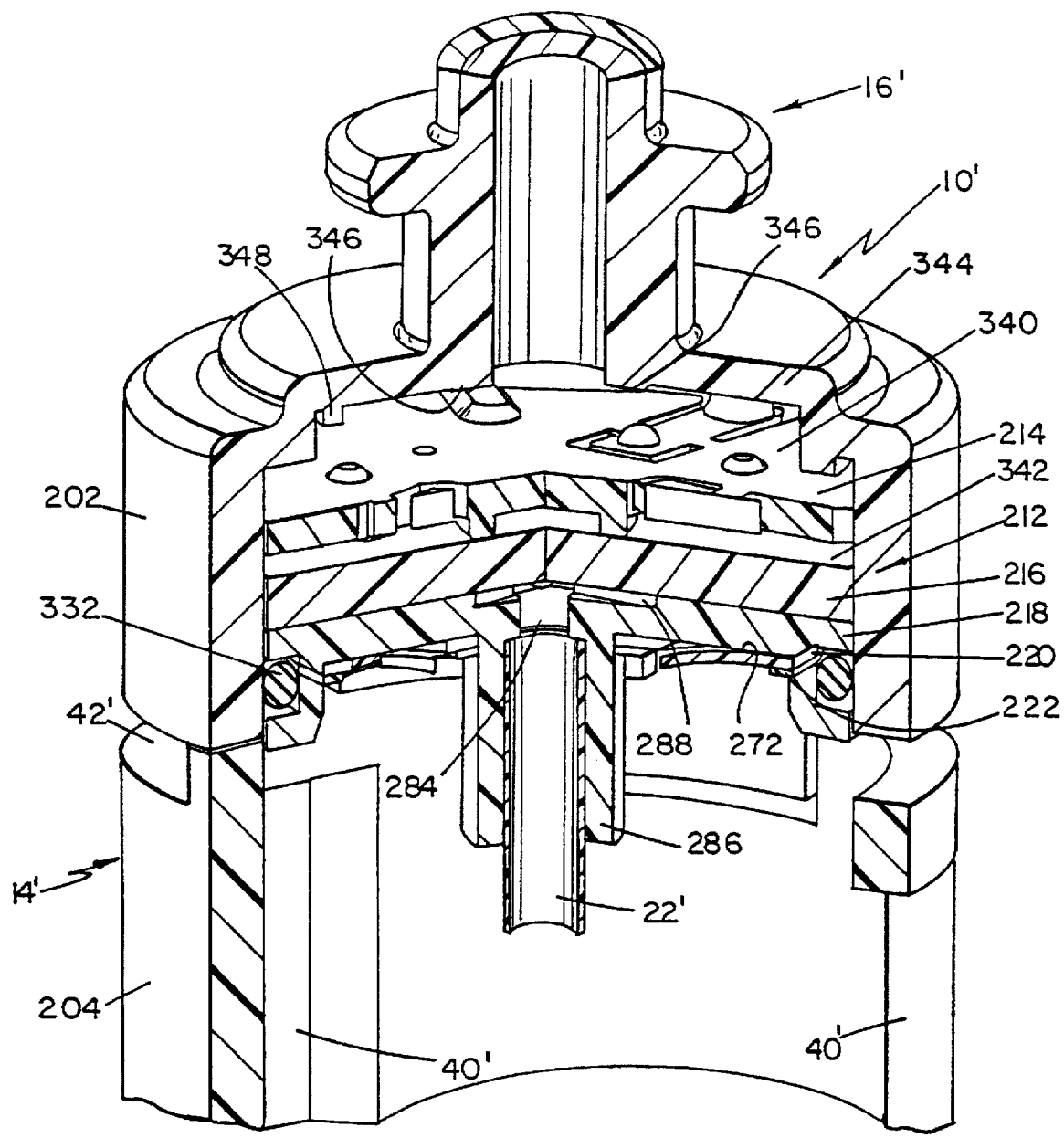
FIG. 18 is a sectional perspective view of a second embodiment of the variable oxygen concentration high-flow nebulizer of the present invention.

FIG. 18 illustrates a second embodiment of the variable oxygen concentration high-flow nebulizer 10' of the present invention. For ease of reference, like elements of the second embodiment 10' will have identical reference numerals including a prime ("'") The second embodiment of the nebulizer 10' includes a cylindrical nebulizer housing 14' having a pressurized gas inlet 16' and an outlet (not shown). A conventional screw cap (not shown) is optionally attached to the pressurized gas inlet 16'. The dip tube 22' (or liquid supply tube) descends from the bottom of the nebulizer components. A flow control collar having an ambient air window and an adjustment lever as illustrated in FIG. 1 is intended to be used with the second embodiment of FIG. 18, although it is not illustrated for the sake of clarity. The second embodiment 10' generally functions in a manner similar to the first embodiment 10 described above, although the internal components are configured quite differently for ease of manufacture.

Figure 19:
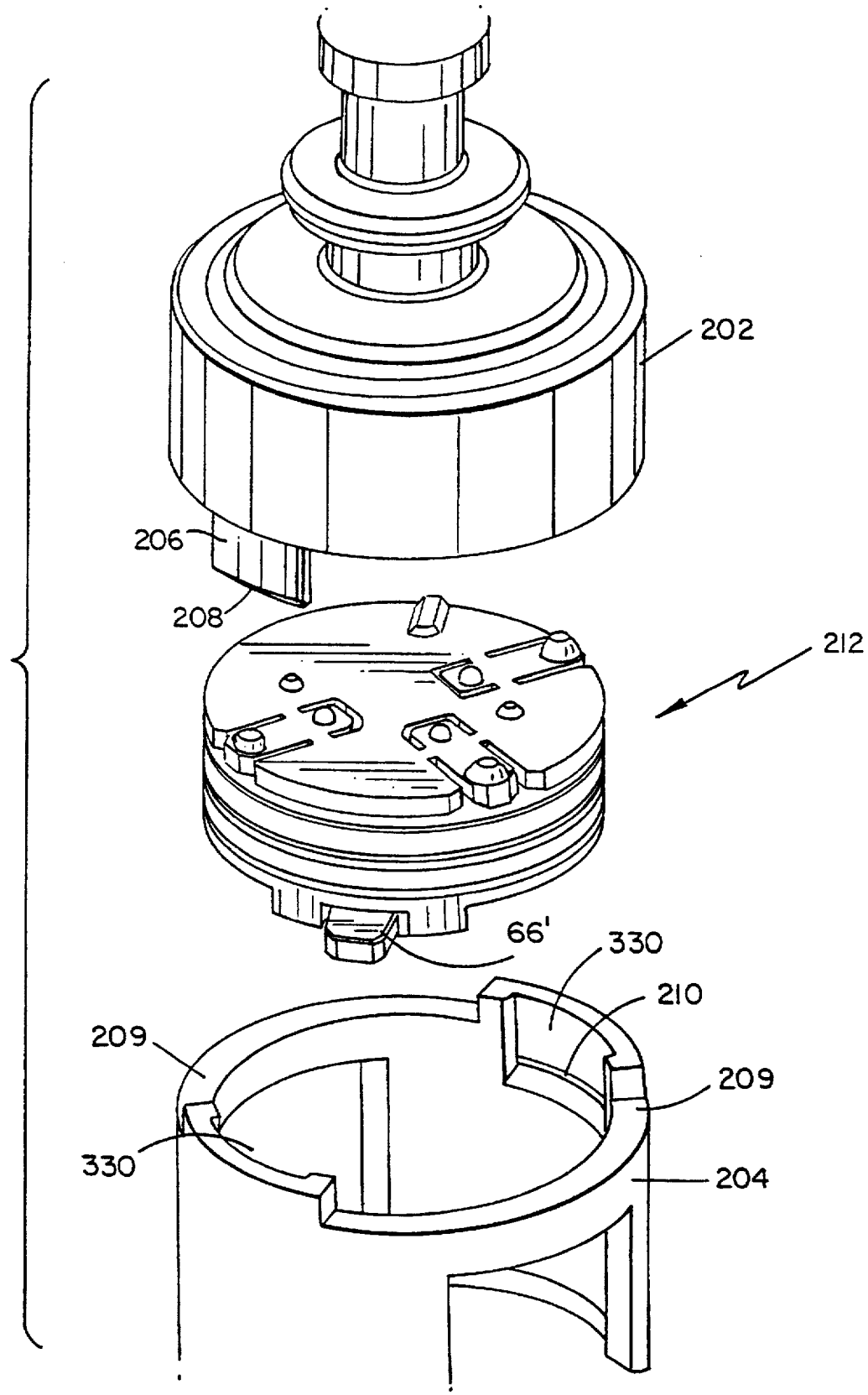
FIG. 19 is a partial exploded view of the nebulizer of FIG. 18.

With continued reference to FIG. 18 and FIG. 19, the cylindrical housing 14' includes a top 202 and a bottom 204. The cylindrical top 202 and the cylindrical bottom 204 are held together with a pair of clips 206 (one shown) on opposite sides of the housing top 202. The clips 206 include an arcuate lip 208 which engages an arcuate depression 210 on an inner surface of the cylindrical housing bottom 204. A pair of voids 209 in the top edge of the bottom 204 form the arcuate slots 42' between the housing top 202 and the housing bottom 204. Residing within the cylindrical housing top 202 is a disk assembly 212. The disk assembly 212 consists of a valve disk 214, a primary nozzle disk 216, a secondary nozzle disk 218, a gasket 220 and a retainer 222 which are sandwiched together in an abutting relationship.

Figure 20:
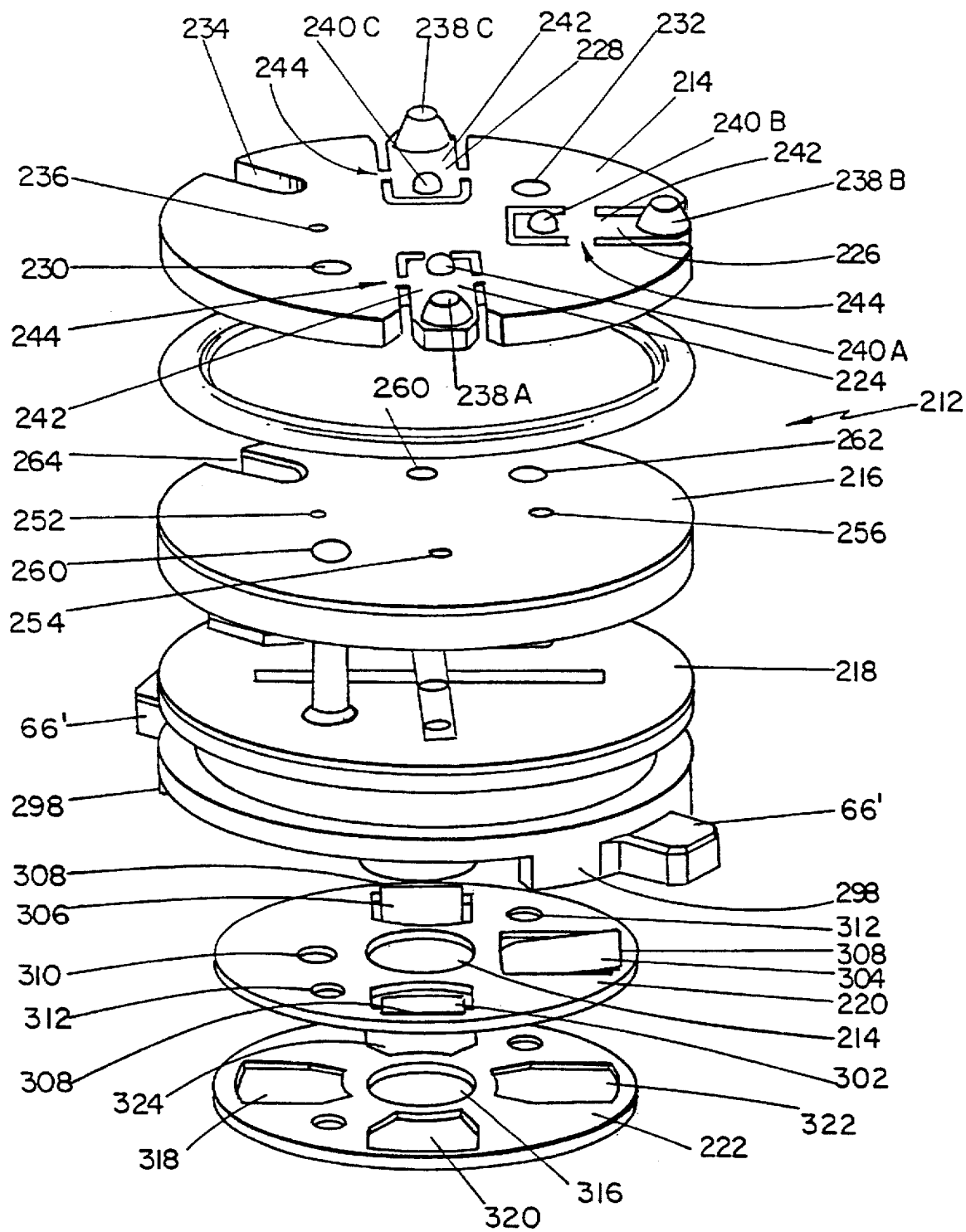
FIG. 20 is an exploded perspective view of the disk assembly of the nebulizer of FIG. 18.
Figure 21:
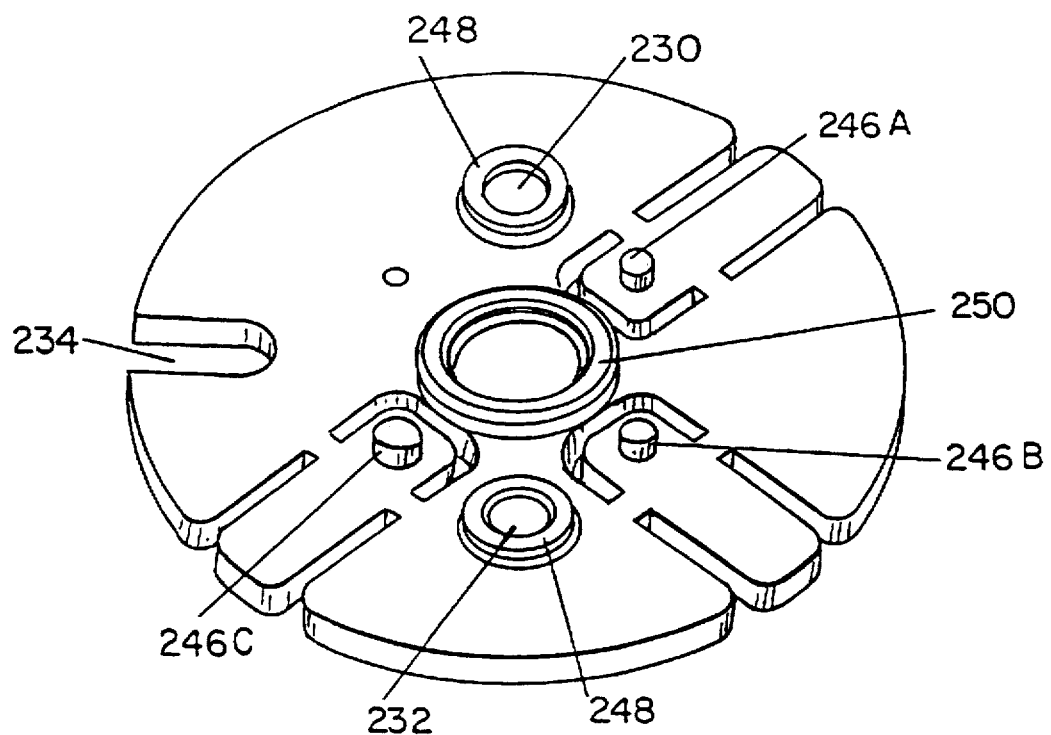
FIG. 21 is a perspective bottom view of the valve disk of the nebulizer of FIG. 18.
Figure 23:
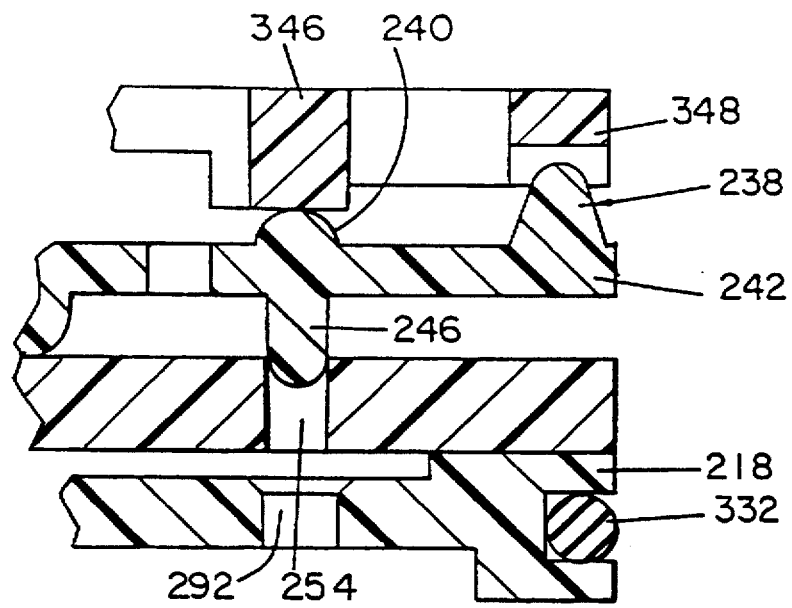
FIG. 23 illustrates a valve occluding a primary nozzle.

FIG. 20 illustrates the disk assembly 212 in an exploded view. The valve disk 214 is integrally molded from a semi-rigid thermoplastic such as polyethylene or polypropylene. The valve disk 14 includes a second primary nozzle valve 224, a third primary nozzle valve 226 and a fourth primary nozzle valve 228. The valve disk 214 also includes first and second keying holes 230, 232 and optionally a keying slot 234, the functions of which will be discussed below with regard to construction of the disk assembly 212. The valve disk 214 also includes a pressurized gas hole 236. Each of the second, third and fourth primary nozzle valves, 224, 226, 228 is integrally molded with the valve disk 214 and includes a valve opening cam 238A, 238B, 238C and a valve closing cam 240A, 240B, 240C extending upward on opposite ends of an elongate lever 242 which pivots about an integral hinge 244. The opening valve cams 238A, 238B, 238C of the second, third and fourth primary nozzle valves extend increasing amounts for reasons which will be discussed below with regard to the valve actuator profile, FIG. 25. Referring to FIG. 21, a plug 246A, 246B, 246C descends from the bottom of the elongate lever 242 underneath the valve closing cam 240 (see FIGS. 25 and 26). These plugs are of a size to occlude a corresponding primary nozzle, as illustrated in FIG. 23. With further reference to FIG. 21, an annular spacer 248 surrounds each of the first keying hole 230 and second keying hole 232 and an annular spacer 250 extends from the center of the bottom of the valve disk.

Figure 24:
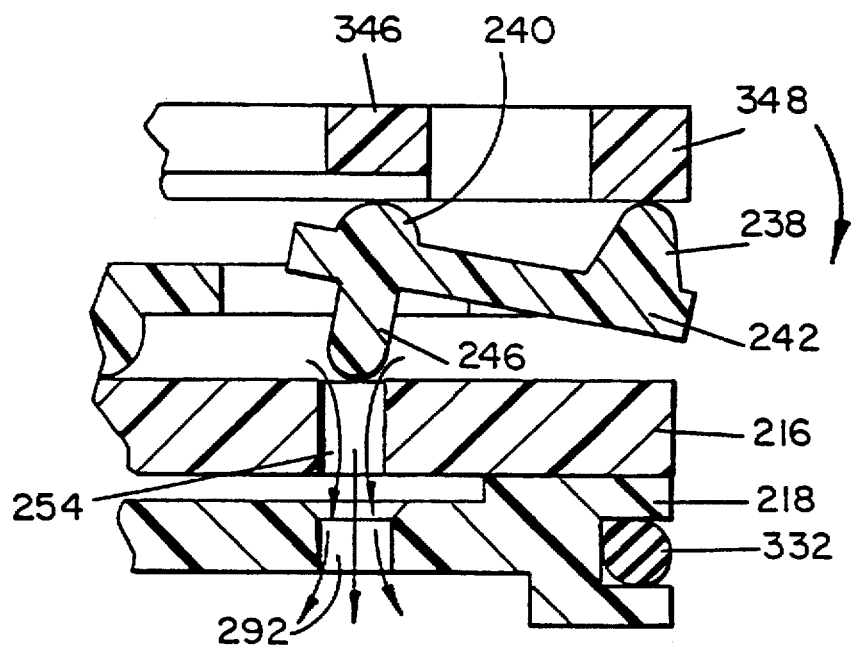
FIG. 24 illustrates a valve recruiting a primary nozzle.
Figure 25A:
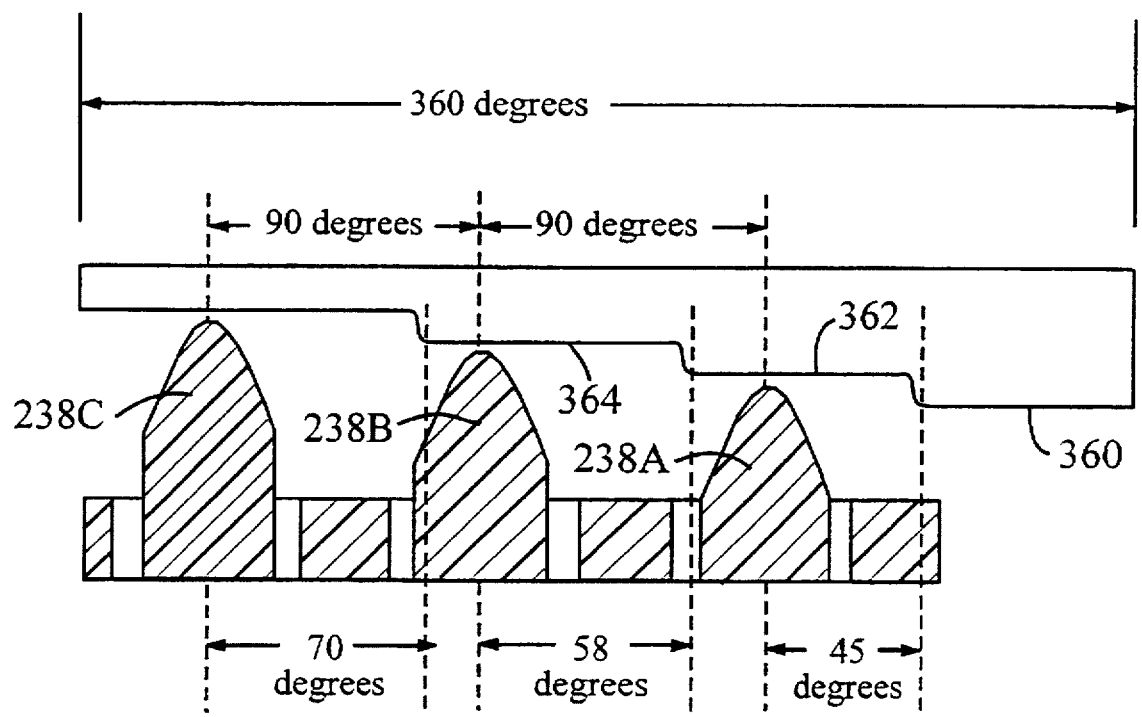
FIG. 25 A-E are a linear depiction of the arcuate valve actuator interacting with the second, third and fourth valve cams.
Figure 25B:
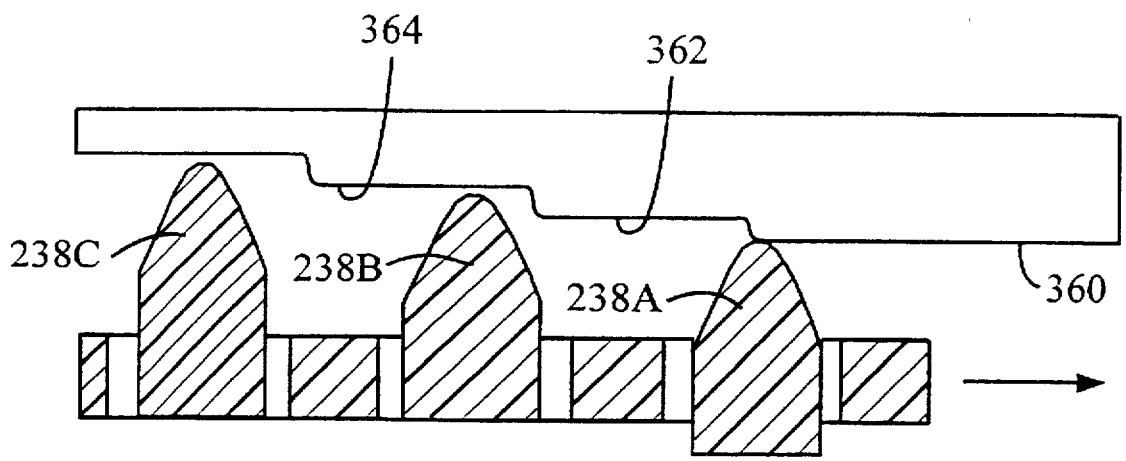
Figure 25C:
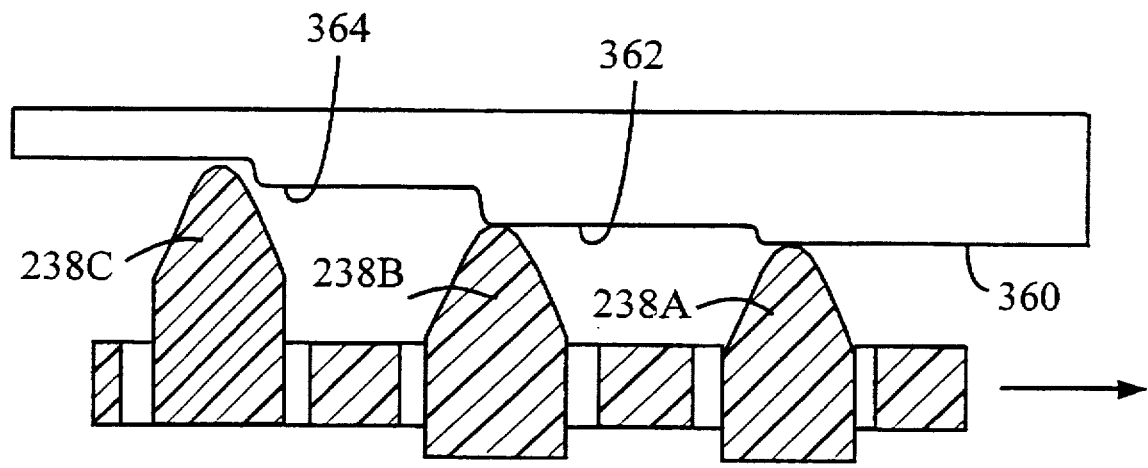
Figure 25D:
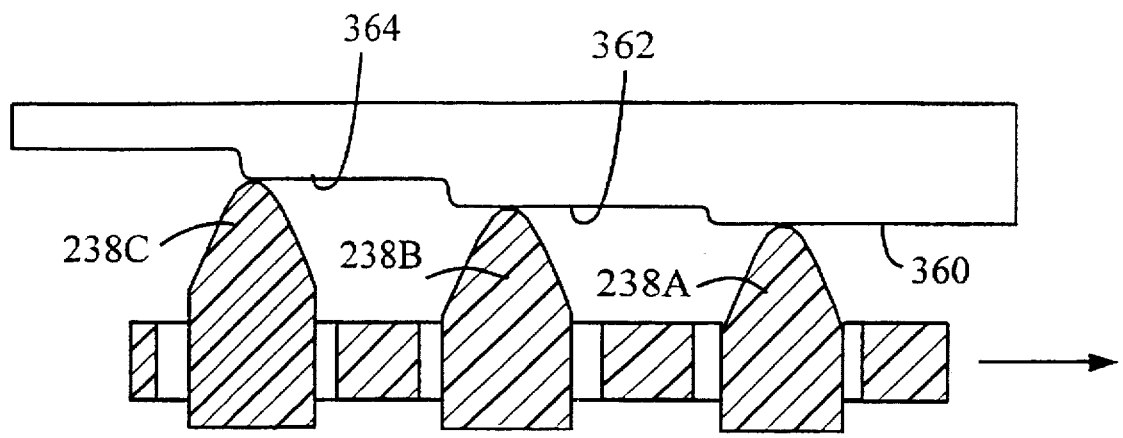
Figure 25E:
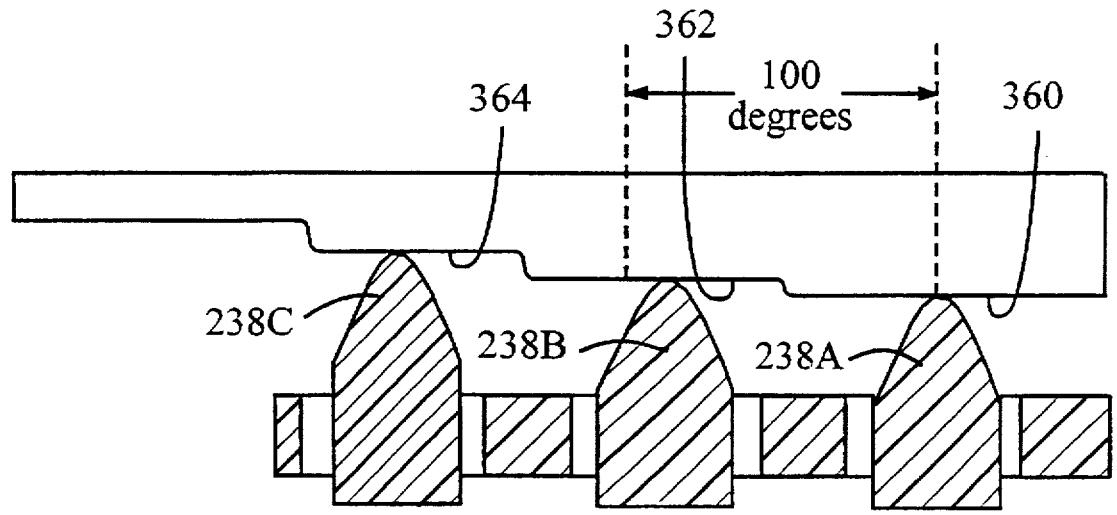

The primary nozzle disk 216 is viewed from the top in FIG. 20 and includes a first primary nozzle 252, a second primary nozzle 254, a third primary nozzle 256 and a fourth primary nozzle 258 of increasing diameters. Each of the first, second, third and fourth primary or gas nozzles merely constitute holes through the primary nozzle disk 216 as best illustrated in FIGS. 23 and 24 with nozzle outlet at the bottom of the primary nozzle disk. As with the valve disk 214, the primary nozzle disk 216 also includes first and second keying holes 260, 262 and an optional keying slot 264. The primary nozzle disk 216 is preferably made of a thermoplastic such as polyethylene or polypropylene which can be readily bonded to the annular spacers 248, 250 of the valve disk by ultrasonic welding, chemical welding, heat bonding or the like, which will be discussed in greater detail below.

Figure 22:
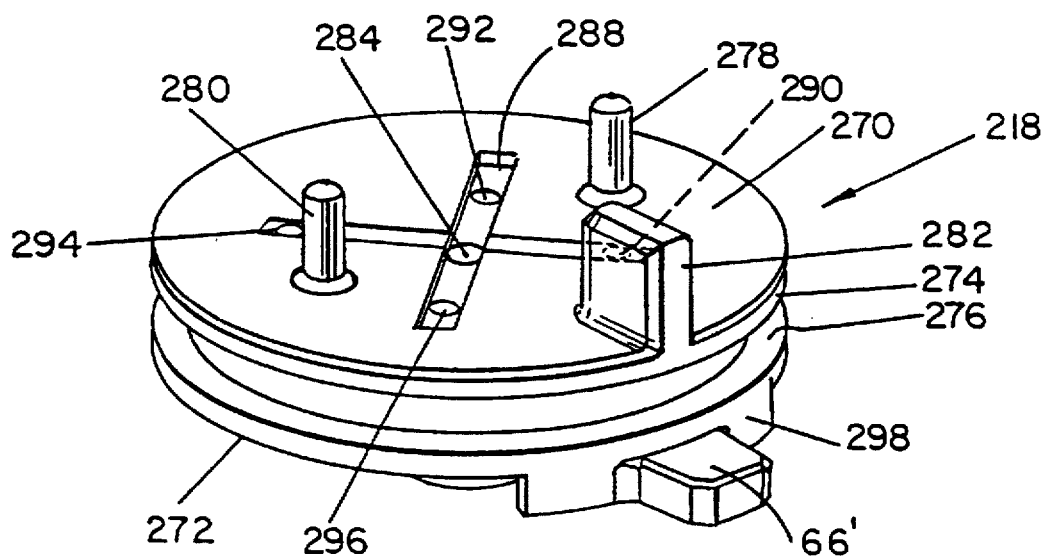
FIG. 22 is a perspective top view of the secondary nozzle disk of the nebulizer of FIG. 18.

The secondary nozzle disk 218 is most clearly illustrated in FIG. 22 and it also is integrally molded from a thermoplastic such as polyethylene or polypropylene. The secondary nozzle disk 218 has a disk top 270, a disk bottom 272 and a side wall 274. An annular O-ring slot 276 is formed in the side wall 274. From the secondary nozzle disk top 270 extends a first key 278, a second key 280 and an optional rectangular key 282. The first and second keys 278, 280 are sized to fit snugly in the first and second keying holes 230, 232 of the valve disk 214 and the first and second keying holes 260, 262 of the primary nozzle disk 216. Preferably the first and second keying holes 230, 232 and the first and second keys 278, 280 are of distinct size or cross-sectional shape to facilitate proper alignment of the disks 214, 216, 218. Alternatively or in addition, the rectangular key 282 can be provided both to facilitate alignment and to strengthen the disk assembly 212. At the center of the disk top 270 is a liquid supply hole or liquid conduit 284 which is a hole that extends between the disk top 270 and disk bottom 272. Referring to FIG. 18, from the secondary nozzle disk 218 bottom 272 an annular sleeve 286 extends around the liquid conduit 284.

Referring back to FIG. 22, a cross slot 288 is formed in the disk top 270 with the center of the cross being the liquid conduit 284. Proximate the end of each arm of the cross slot 288 is the first secondary nozzle 290, the second secondary nozzle 292, the third secondary nozzle 294 and the fourth secondary nozzle 296. As discussed below, with the disk assembly 212 assembled, the first, second, third and fourth secondary nozzles 290, 292, 294, 296 align with the first, second, third and fourth primary nozzles 252, 254, 256, 258 (see e.g. FIG. 23). An arcuate flange 298 extends downward from the bottom 272 of the secondary nozzle disk 218 on opposite sides along a portion of the circumference of the disk bottom 272. A connector arm 66' extends radially from each of the flanges 298.

Referring to FIG. 20, the gasket 220 consists of second, third and fourth flap valves 302, 304, 306 joined to the valve body 220 by a living hinge 308. The gasket 220 is preferably made of a flexible mataerial such as silicone rubber. The second, third and fourth flap valves 302, 304, 306 correspond to the second, third and fourth secondary nozzles 292, 294 and 296, respectively. A hole 310 corresponds to the first secondary nozzle 290. A pair of keying holes 312 receives keys which extend from the bottom 272 of the secondary nozzle disk 218 (but which are not shown). Finally, the disk 220 includes at its center a hole 214 dimensioned to receive the annular sleeve 286 of the secondary nozzle disk 218.

With continued reference to FIG. 20, the retainer 222 comprises at its center a first hole 216 for receiving the annular sleeve 286 and first, second, third and fourth voids 218, 220, 222, 224 which correspond to the second, third and fourth flap valves 302, 304, 306 and the hole 310. Finally, the retainer 222 includes keying holes 226 corresponding to the keying holes 310 of the flap gasket 220. The retainer 222 is integrally molded from the same material as the valve disk 214, the primary nozzle disk 216 and the secondary nozzle disk 218.

The disk assembly is sandwiched as illustrated in FIG. 20 and heat staked, solvent bonded or ultrasonically bonded into a disk assembly 212 illustrated in FIG. 19. As discussed above, the first and second keys 278, 280 provide for proper orientation and alignment of the disks 214, 216, 218. Following bonding of the disks into the disk assembly 212, the O-ring 332 is fed into the annular O-ring slot 276 of the secondary nozzle disk 218. This disk assembly 212 is then placed between the cylindrical housing top 202 and cylindrical housing bottom 204 with the connecting arms 66' resting on the voids 209 in the cylindrical housing bottom which defined the arcuate slots 42'. The cylindrical housing top 202 is then aligned with the clips 206 in the guides 330 and the cylindrical housing top 202 and cylindrical housing bottom 204 are snapped together, retaining the disk assembly 212 therebetween as best illustrated in FIG. 18.

Referring to FIG. 18, the heat staking of the disk assembly results in the annular spacers 248, 250 of the valve disk 214 being bonded to the top of the primary nozzle disk 216. The bottom of the primary nozzle disk 216 is bonded to the top 270 of the secondary nozzle disk 218 in fluid tight engagement so that the cross slots 288 define fluid tight closed disk conduits.

With the disk assembly 212 installed as illustrated in FIG. 18, high pressured gas from the inlet 16' fills the void 340 above the valve disk and is free to flow between the valves 224, 226, 228 and through the pressurized gas hole 236 into the plenum 342 defined between the valve disk 214 and the primary nozzle disk 212 by the annular spacers 248, 250. The high pressured gas is prevented from accessing the cross slots 288 by the bonding discussed above. The O-ring 232 provides a fluid tight seal that prevents leakage of the high pressured gas between the disk assembly and the wall 40' of the nebulizer housing 14.

Figure 26:
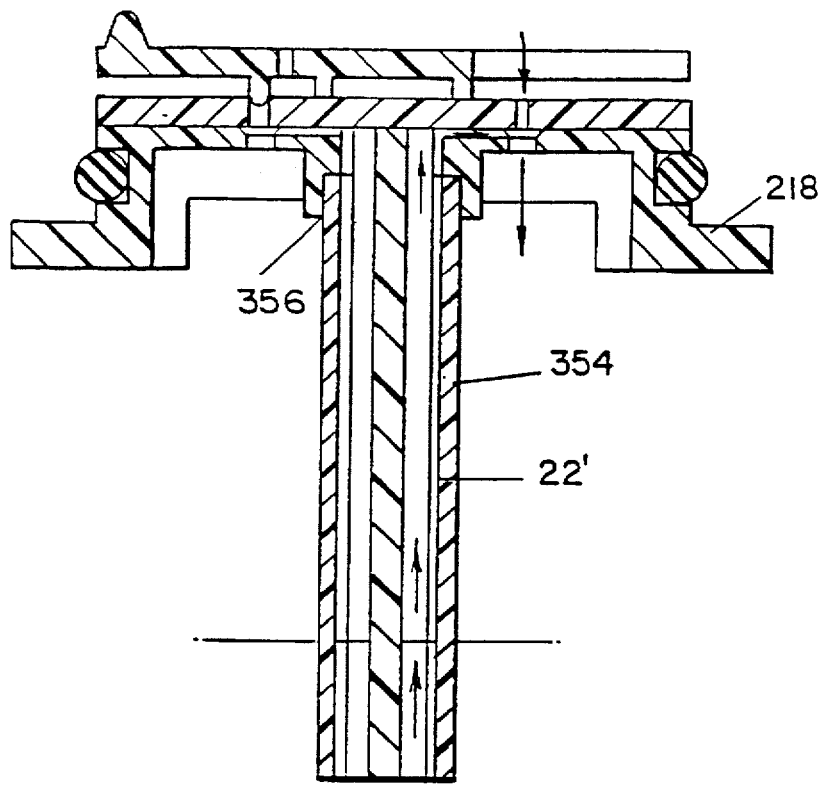
FIG. 26 is a cross sectional side view of an alternate embodiment of a liquid delivery structure for use in the nebulizer of FIG. 18.
Figure 27:
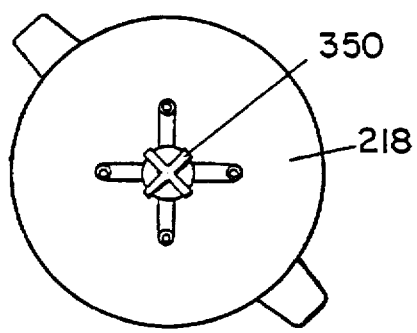
FIG. 27 is a bottom view of the secondary nozzle disk of the alternate embodiment of FIG. 26.
Figure 28:
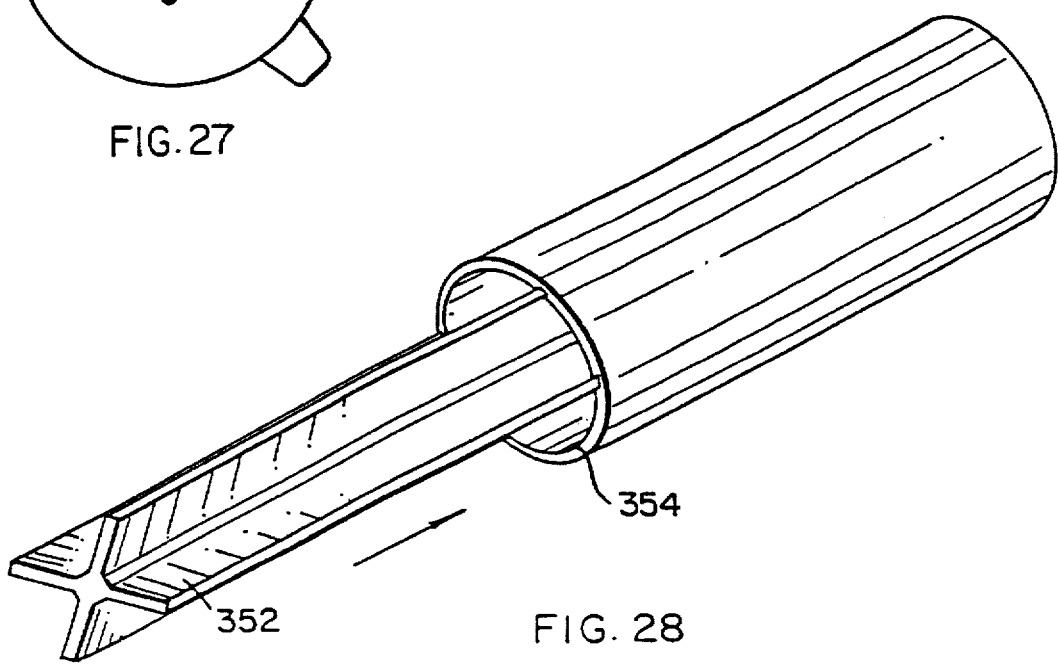
FIG. 28 illustrates the construction of a dip tube for use in the alternate embodiment of FIG. 26.

In operation, pressurized gas enters the inlet 16' fills the void 340 and the plenum 342. The first primary nozzle 252 is not valved so high pressure gas always flows through the first primary valve 252 and the first secondary valve 290. The high velocity of the oxygen at the first primary nozzle 252 creates a negative pressure at the first secondary nozzle which draws liquid up the dip tube 22' from a liquid reservoir (not shown) through the liquid conduit 284 and into the cross-slots 288. When only the primary valve is recruited, the same negative pressure which draws the fluid into the dip tube 22' for nebulization also causes the second, third and fourth flap valves 102, 104, 106 to be drawn over the second, third and fourth secondary nozzles to seal the nozzles against aspiration of air to maintain the vacuum.

Although not illustrated with regard to the second embodiment of the variable oxygen concentration high-flow nebulizer 10', as with the first embodiment 10, the connecting arms 66' extend through the arcuate slots 42' and engage with a flow control collar (not shown) having ambient air windows which can be brought into and out of alignment with the ambient air vents 40'. In the manner which will be discussed in greater detail below, as the flow control collar 24 is rotated counter-clockwise (with respect to the top of the nebulizer housing 14'), the ambient air vents 40' become blocked by the flow control collar. However, as with the first embodiment, in order to maintain an adequate total flow -of gases, as the flow control collar is rotated further counterclockwise eventually the second, then the third and the fourth primary nozzles are recruited as the ambient air vents 40' are blocked, thereby maintaining a total flow of nebulized gas above an acceptable minimum while allowing for control of the oxygen concentration to vary between about 28% and 100% inspired oxygen. This is illustrated graphically at FIGS. 16 and 17 and explained more thoroughly below.

Descending from the inside surface of the top 344 of the housing 14' is an inner stepped cam actuator 346 and an outer stepped cam actuator 348. While these stepped inner and outer cam actuators are annular, the profile of the outer cam actuator 348 and its interaction with the valve opening cam 238A, 238B, 238C is shown linearly in FIGS. 25A–25E. This is representative of the inner cam actuator and the valve closing cams 240A, 240B, 240C. With the collar 24 positioned so that the air entrainment vents 40' are not blocked, the valve opening cams 238A, 238B and 238C are aligned as indicated in FIG. 25A with respect to the outer cam actuator 348. In this position, none of the valve opening cams 238A, 238B or 238C are actuated by the outer cam actuator 248. Upon rotation of the collar 24 counterclockwise as viewed looking down on FIG. 18 approximately 45°, the first stepped surface 360 of the upper cam actuator 348 engages the valve opening cam 238A of the second primary nozzle valve 224 and depresses it. Simultaneously, the inner stepped cam actuator 146 no longer contacts the valve closing cam 240A. This causes the elongate lever 242 to pivot about the integral hinge 244 to remove the plug 246 from the second primary nozzle 254, as illustrated in FIG. 24. In turn, the pressurized air flowing through the second primary nozzle 254 creates a negative pressure drawing liquid for nebulization into the corresponding arm of the cross-slot 288 to the second secondary nozzle 292. The force of the pressurized air also biases open the second flap valve 302. Rotation of the collar clockwise will in turn cause the inner stepped cam actuator 346 to contact the valve closing cam 240A while the outer stepped cam simultaneously ceases to contact the valve opening cam 348, allowing the plug 246 to be driven into the second primary nozzle 254 so as to prevent the flow of gas through the second primary nozzle 254. See FIG. 23. This in turn stops the flow of the liquid through the cross-slot 282A and allows the vacuum created by the first primary nozzle 252 to draw the flap valve 302 into abutment with the second secondary nozzle 292. As illustrated in FIG. 25C, further rotation of the collar 24 an additional 13° counterclockwise causes the second stepped surface 262 of the outer cam actuator 348 to depress the valve opening cam 238B of the third primary nozzle valve 226 while the inner stepped cam actuator disengages the valve closing cam 242B, thereby recruiting the third nozzle. Referring to FIG. 25D, an additional 12° counterclockwise rotation of the collar 24 causes the third stepped surface 364 to engage the valve opening cam 238C, thereby recruiting the fourth primary nozzle. The collar 24 can be rotated another 30° for total rotation of approximately 100°, whereupon the air entrainment vents 40' will be completely blocked and pure oxygen will be supplied to a patient. This actuation is controlled in such a manner that the percentage of inspired oxygen per degree of rotation is varied in the manner discussed below with regard to FIGS. 16 and 17. Thus, the principle distinction between the first and second embodiments of the nebulizer 10, 10' is the disk structure of the second embodiment 10'. Both structures provide varying concentrations of oxygen while maintaining an adequate flow of respiratory gasses.

As an alternative to providing the gasket 220 and retainer 222, a partitioned dip tube 22' can be used which provides four liquid supply conduits 370A–370D, with a liquid supply channel corresponding to each of the liquid supply channels 288, as illustrated in its assembled form in FIG. 26. More particularly, in this embodiment the bottom of the secondary nozzle disk 218 has a cross slit 350 which receives the walls of the interior partition 352 of the dip valve. The dimensions of the dip tube 22' with the interior partition 352 are such that, referring to FIG. 26, the outer wall 354 of the dip tube mates 22' with an inner step 356 of the annular sleeve 286 while the protruding end of the interior partition 352 is received in the cross slits 350. When assembled in this manner, each conduit 370A–370D defined by the interior partition 352 is essentially like a separate dip tube, thereby negating the need for the flapper valves discussed above. Thus, with only the first pair of nozzles recruited, fluid would be drawn into the corresponding fluid conduit while no liquid would be drawn into the other channels until their corresponding valves are recruited. The dip tube 22' can be extruded with the partition 352 or the partition 352 may be inserted and then bonded to an inner surface of the outer wall 354.

As viewed in FIG. 10 with respect to the first embodiment, the first, second, third and fourth primary nozzles (102, 104, 106, 108) are of increasing diameter, as described above. The same is true with respect to the second embodiment as illustrated in FIG. 20. Conventional nebulizers used in the medical field have total gas flows ranging from 100 liters per minute at a 28% oxygen setting to 8–10 liters per minute at 100% oxygen. This results because as the oxygen setting on the nebulizer is increased the effective size of the air entrainment vents 40 is reduced while the flow through the oxygen nozzle is constant, therefore decreasing the total gas flow to the patient. The variable oxygen concentration high-flow nebulizer maintains the necessary flow of respiratory gasses by recruiting additional nozzles of increasing effective diameter as the ambient air vents 40 are closed. The diameters of the nozzles are calculated to maintain an acceptable minimum amount of total gas flow to a patient (40 liters per minute or more when connected to a 50–60 psig oxygen source).

Figure 16:
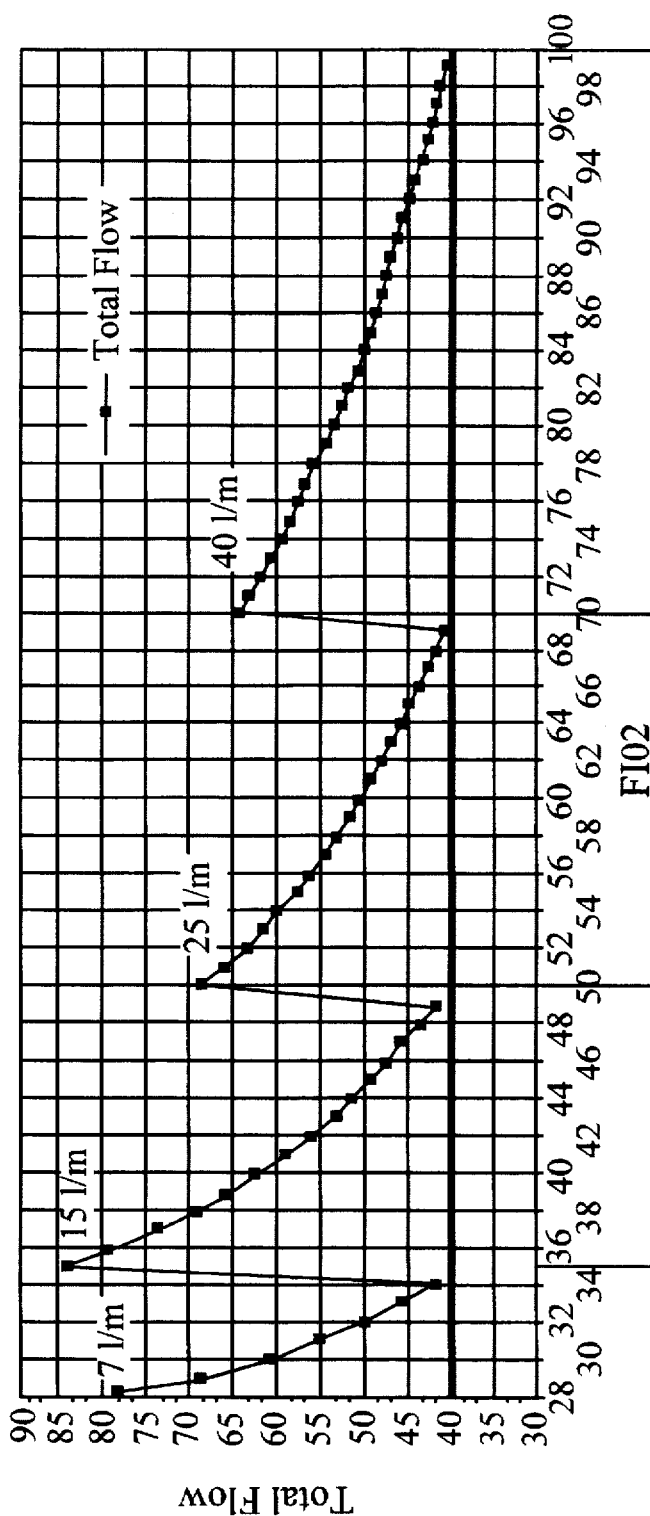
FIG. 16 is a graph of total flow of respiratory gas versus percent of inspired oxygen (FIO2) for the variable oxygen concentration high-flow nebulizer.

FIG. 16 is a graph of the total flow of the nebulizer as a function of percentage of oxygen in the respiratory gas stream. FIG. 17, immediately below FIG. 16, is a diagram of the degree of rotation of the collar relative to the nebulizer housing 180 indicating plunger travel 182 and the point at which the various nozzles are recruited. In operation, a clinician need only connect the pressurized gas inlet to a source of pressurized oxygen at about 50 psig, as discussed above. The pressurized oxygen source valve is then fully opened (or adjusted to "flush"). As discussed below, the variable oxygen concentration high-flow nebulizer then self-adjusts the oxygen flow rate to maintain the desired total gas flow, thereby relieving the clinician from having to further adjust the pressurized oxygen source valve, which both improves ease of use of the nebulizer as well as patient safety. Moreover, a separate flow meter is not required in association with the pressurized oxygen source for the nebulizer to be used safely and effectively.

With just the first nozzle recruited the total flow of oxygen is 7 liters per minute at a fraction of inspired oxygen (FI02) of 28%. Total flow from the outlet of the nebulizer is calculated as follows:

$$\text{Total Flow} = \frac{\text{O2 Flow} \times 0.78}{\text{FI02} - 0.21}, \text{ or } \frac{7 \text{ l/m} \times 0.78}{0.28 - 0.21} = 78 \text{ l/m}.$$

The 0.78 is the percentage of nitrogen in air and the 0.21 is the percentage of oxygen in air. If the oxygen flow remains constant, the total flow diminishes as the FI02 increases. FIG. 16 thus indicates that as the ambient air vents 40 are constricted, thereby increasing the FI02, the total flow of gas quickly diminishes to around 40 l/m of an FI02 of 34, at which point the second nozzle is recruited.

When the second nozzle is recruited the total flow of oxygen increases to 15 l/m, increasing the total flow to 84 l/m. As the FI02 approaches 50 the total gas flow quickly diminishes to 40 l/m until the third nozzle is recruited at FI02 of 50. The flow of oxygen then increases to 25 liters per minute with a total flow of 67 l/m. As the FI02 approaches 70 the total gas flow again diminishes to around 40 l/m when the fourth and final nozzle is recruited and the oxygen flow increases to 40 liters per minute, thus assuring that even at a FI02 of 100% oxygen concentration the total flow of respiratory gas to a patient will not decrease below 40 liters per minute.

The variable oxygen concentration high-flow nebulizer described herein provides for concentrations of inspired oxygen between 28–100% while maintaining the flow rate to a patient at least 40 liters per minute. The variable oxygen concentration high-flow nebulizer therefore eliminates the need to provide the multiple nebulizers in parallel in order to provide adequate flow volume to a patient. The variable oxygen concentration high-flow nebulizer further automatically recruits additional nozzles as the ambient air vent is closed to maintain the required flow rate. The carrier gas supply and liquid supply are simultaneously recruited and terminated as the effective size of the ambient air vent decreases and increases, respectively. Thus, the nebulizer provides for essentially fool proof and accurate delivery of a desired oxygen concentration with a simple turn of the flow control collar without risk of denying a patient a required flow rate of respiratory gas. The variable oxygen concentration high-flow nebulizer requires only a standard 50 psig oxygen connection, so it is usable in most hospital, sub-acute hospital and home care settings. The first embodiment of the nebulizer 10' consists of only six principal components which can be readily injection molded from thermoplastic. The second embodiment consists of only 8 or 10 injection molded and easily assembled components. As a result, both embodiments of the nebulizer can be manufactured and assembled quickly, easily and inexpensively. The relatively few moving parts results in a highly reliable, easy to use nebulizer. Finally, because only a single nebulizer is required to provide a very wide range of oxygen concentrations, hospitals using the variable oxygen concentration high-flow nebulizer will not be required to stock several nebulizer models to meet their various patient's needs. Furthermore, as an individual patient's requirement for oxygen concentration varies during application of a therapy, the nebulizer need not be replaced, possibly interrupting a critical therapy, but merely adjusted by a simple turn of the flow control collar.

What is claimed is:

1. A nebulizer for providing a select rate of flow of a gas entraining a nebulized liquid, the nebulizer comprising:

at least two gas nozzles, each gas nozzle having a gas outlet;

gas connecting means for connecting in fluid communication a pressurized carrier gas supply and each gas nozzle;

a liquid outlet corresponding to each gas nozzle positioned proximate to the gas outlet of the corresponding nozzle for nebulization of liquid from the liquid outlet in a stream of carrier gas flowing from the gas outlet of each nozzle;

means for connecting in liquid communication each liquid outlet and a liquid supply;

gas adjustment means in fluid communication with at least one of the gas nozzles for selectively recruiting the at least one gas nozzle and preventing gas from flowing from the at least one gas nozzle; and at least one other gas nozzle being independent of the gas adjustment means to provide a continuous flow of gas.

2. The nebulizer of claim 1 further comprising liquid control means operatively associated with the liquid communication means for selectively allowing and preventing flow of liquid through a select liquid outlet.

3. The nebulizer of claim 2 further comprising coordinating means operatively associated between the liquid control means and the gas adjustment means for causing the liquid control means to prevent flow of liquid through a liquid outlet when the gas adjustment means selectively prevents gas from flowing from a corresponding gas nozzle and for causing the liquid control means to allow flow of liquid through the liquid outlet when the gas adjustment means selectively recruits the gas nozzle.

4. The nebulizer of claim 3 comprising a plurality of gas nozzles and a corresponding plurality of liquid outlets, each liquid outlet positioned proximate to a distinct gas nozzle to define liquid outlet gas nozzle pairs, the coordinating means coordinating gas and liquid flow through the liquid outlet gas nozzle pairs.

5. The nebulizer of claim 3 further comprising:

a housing having a wall and a mixing chamber within the wall for receiving gas and nebulized liquid from the gas outlet and corresponding liquid outlets, the wall having at least one ambient air vent for providing a flow of ambient air into the mixing chamber and an outlet for exhausting the nebulized liquid, gas and ambient air;

vent control means for selectively varying the effective size of the ambient air vent between fully open and fully closed; and linking means for linking the gas adjustment means and the vent control means so that as the vent control means is adjusted to decrease the effective size of the vent the gas adjustment means automatically increases the number of recruited nozzles and as the vent control means is adjusted to increase the effective size of the vent the gas adjustment means automatically decreases the number of recruited nozzles.

6. The nebulizer of claim 1 wherein the gas adjustment means comprises:

a cylinder having first and second ends and a hole through the cylinder wall corresponding to each gas nozzle, each hole being spaced lengthwise along the cylinder wall between the first and second ends;

a conduit connecting each hole to the corresponding nozzle inlet;

a plunger disposed within the cylinder, the plunger having a cylindrical side wall with one end open and the other end closed to define a fluid plenum, the outer diameter of the plunger being less than the inner diameter of the cylinder to define an annular space therebetween, the plunger including an orifice in the side wall between the fluid plenum and outside the fluid plenum, the plunger further including means between the closed end and the orifice for forming a fluid tight seal between the interior of the cylinder and the side wall of the plunger, the gas connecting means being in fluid communication with the open end of the plunger; and means for selectively moving the plunger within the cylinder in a first lengthwise direction to recruit select nozzles by moving the sealing means between the hole corresponding to the nozzle and the second end of the cylinder and in a second lengthwise direction to prevent flow to select nozzles by moving the sealing means between the corresponding hole and the first end of the cylinder.

7. The nebulizer of claim 6 wherein the selectively moving means comprises threads in an interior surface of the cylinder, thread engaging means on the plunger and means for preventing the plunger from rotating with the cylinder, whereby relative rotation between the cylinder and the plunger in a first rotational direction will cause the plunger to move lengthwise toward the second end of the cylinder and relative rotation in a second rotational direction will cause the plunger to move lengthwise away from the second end of the cylinder.

8. The nebulizer of claim 6 further comprising:

a housing having a wall and a mixing chamber within the wall for receiving gas and nebulized liquid from the gas outlet and associated liquid outlets, the wall having at least one ambient air vent for providing a flow of ambient air into the mixing chamber and an outlet for exhausting the nebulized liquid, gas and ambient air;

a collar having a wall enveloping a portion of an outer surface of the housing, the collar including a window for selectively varying the effective size of the ambient air vent between fully open and fully closed by varying the extent to which the window is aligned with the vent; and connecting means between the collar and the plunger for moving the plunger in the first lengthwise direction as the effective size of the air vent is closed and for moving the plunger in the second lengthwise direction as the effective size of the air vent is opened.

9. The nebulizer of claim 7 further comprising:

a cylindrical housing having a wall and a mixing chamber within the wall for receiving gas and nebulized liquid from the gas outlet and associated liquid outlets, the wall having at least one ambient air vent for providing a flow of ambient air into the mixing chamber and an outlet for exhausting the nebulized liquid, gas and ambient air;

a cylindrical collar having a wall enveloping a portion of an outer surface of the housing, the collar including a window for selectively varying the effective size of the ambient air vent between fully open by rotation of the collar relative to the housing in a first rotational direction to align the window and vent and fully closed by rotation of the collar in a second opposite rotational direction to put the window and vent in an unaligned position; and connecting means between the cylindrical collar and the plunger for moving the plunger in the second lengthwise direction relative to the cylinder as the cylindrical collar is rotated in the first lengthwise rotational direction and for moving the plunger in the first direction relative to the cylinder as the cylindrical collar is rotated in the second rotational direction.

10. A nebulizer for providing a select rate of flow of a gas entraining a nebulized liquid the nebulizer comprising:

at least two gas nozzles each gas nozzle having a gas outlet, gas connecting means for connecting in fluid communication a pressurized carrier gas supply and each gas nozzle:

a liquid outlet corresponding to each gas nozzle positioned proximate to the gas outlet of the corresponding nozzle for nebulization of liquid from the liquid outlet in a stream of carrier gas flowing from the gas outlet of each nozzle;

means for connecting in liquid communication each liquid outlet and a liquid supply; an elongate cylindrical housing having a select inner diameter, the gas connecting means being at a closed end of the cylinder; and a gas adjustment means in fluid communication with at least one of the gas nozzles for selectively recruiting the at least one gas nozzle and preventing gas from flowing from the at least one gas nozzle, the gas adjustment means comprising:

a first disk having an outer diameter no greater than the inner diameter of the housing, the first disk having integral valve means actuatable between a recruited and a closed position corresponding to at least one of the at least two gas nozzles for selectively recruiting and closing a corresponding gas nozzle;

means for maintaining the first disk proximate the closed end of the cylinder with the integral valve means in operative association with the at least two gas nozzles; and actuating means on the cylinder operatively associated with the valve means for actuating the valve means between the recruited and closed positions by relative rotation between the first disk and the housing.

11. The nebulizer of claim 10 wherein the integral valve means comprises:

an elongate lever having first and second ends pivotable intermediate the lever ends about an axis perpendicular to its length and parallel to a top surface of the disk;

a valve opening cam on a top surface of the lever proximate the first end of the lever;

a plug proximate the second end of the lever on a bottom surface of the lever; and means for biasing the lever in a closed position with the plug closing a corresponding gas nozzle, the actuating means actuating the valve means to a recruited position by depressing the valve cam, thereby pivoting the lever to a recruited position with the plug spaced from a corresponding gas nozzle.

12. The nebulizer of claim 11 wherein the elongate lever is integrally formed with the disk from a single piece and the biasing means is an integral hinge between the disk and the lever.

13. The nebulizer of claim 11 wherein the biasing means comprises a valve closing cam on the top surface of the lever proximate the second end and a valve closing member on the valve housing, the valve closing member depressing the valve closing cam with the plug closing a corresponding gas nozzle when the actuating means is not depressing the valve cam and the valve closing member disengaging the valve closing cam when the actuating means is depressing the valve cam.

14. A nebulizer for providing a select rate of flow and a select concentration of a gas entraining a nebulized liquid, the nebulizer comprising:

at least two nozzles, each nozzle having a gas outlet;

means for connecting in fluid communication a pressurized gas supply and each nozzle;

a liquid outlet positioned proximate to the gas outlet of each nozzle for nebulization of liquid from the liquid outlet in a stream of gas flowing from the gas outlet of each nozzle;

means for connecting in liquid communication each liquid outlet and a liquid supply;

gas adjustment means in fluid communication with at least one of the gas nozzles for selectively recruiting the at least one gas nozzle and for preventing gas from flowing from the at least one gas nozzle;

a housing having a wall and a mixing chamber within the wall for receiving gas and nebulized liquid from the gas outlets and associated liquid outlets, the wall having at least one ambient air vent for providing a flow of ambient air into the mixing chamber and an outlet for exhausting the nebulized liquid, gas and ambient air; and vent control means for selectively varying the effective size of the ambient air vent between fully open and fully closed.

15. The nebulizer of claim 14 further comprising linking means for linking the gas adjustment means and the vent control means so that as the vent control means is adjusted to decrease the effective size of the vent the gas adjustment means automatically increases the number of recruited nozzles and as the vent control means is adjusted to increase the effective size of the vent the gas adjustment means automatically decreases the number of recruited nozzles.

16. A nebulizer for providing a select rate of flow of a gas entraining a liquid, the nebulizer comprising:

a cylindrical housing having a closed end;

gas connecting means on the closed end of the cylindrical housing for connecting a pressurized gas supply in communication with the cylindrical housing interior;

a primary nozzle disk having at least two gas nozzles, each gas nozzle comprising a hole in the primary nozzle disk defining a gas outlet at a bottom surface of the primary nozzle disk;

first positioning means for positioning the primary nozzle disk proximate but spaced from the closed end of the cylindrical housing;

a valve disk having an outer diameter no greater than the inner diameter of the housing, the valve disk having integral valve means actuatable between a recruited and a closed position corresponding to at lease one of the at least two gas nozzles for selectively recruiting and closing a corresponding gas nozzle;

second positioning means for positioning the valve disk between the primary nozzle disk and the closed end of the cylindrical housing with the integral valve means in operative association with the at least two gas nozzles;

actuating means on the cylinder operatively associated with the valve means for actuating the valve means between the recruited and closed positions by relative rotation between the valve disk and the housing;

a liquid outlet corresponding to each gas nozzle positioned proximate to the gas outlet of the corresponding nozzle for nebulization of liquid from the liquid outlet in a stream of carrier gas flowing from the gas outlet of each nozzle; and means for connecting in liquid communication each liquid outlet with a liquid supply.

17. The nebulizer of claim 16 further comprising:

a secondary nozzle disk having a top and a bottom, the secondary nozzle disk having a hole therethrough forming each of the liquid outlets, the secondary nozzle disk including in its top a slot corresponding to each liquid outlet extending between a common liquid supply hole and each outlet, the secondary nozzle disk top abutting a bottom surface of the primary nozzle disk in a fluid tight relation whereby the slots form fluid tight disk conduits; and a liquid supply tube extending between the common liquid supply hole and a liquid supply, the means for connecting in liquid communication comprising the liquid supply table and the fluid tight disk conduits.

18. The nebulizer of claim 16 further comprising means operatively associated with the liquid communication means for allowing flow of liquid through an outlet when a corresponding gas nozzle is recruited and for preventing flow of liquid through an outlet when a corresponding gas nozzle is closed.

19. The nebulizer of claim 17 wherein the liquid supply tube includes a lengthwise interior partition in liquid tight abutment with the interior of the liquid supply tube, the partition dividing the liquid supply tube into distinct tube conduits corresponding to each disk conduit, and the nebulizer further comprises means for attaching the liquid supply tube to the liquid supply hole with each tube conduit in fluid tight engagement with a distinct disk conduit, whereby liquid will only be delivered to a liquid outlet with the corresponding gas nozzle recruited.

20. The nebulizer of claim 17 further comprising:
a flap valve proximate the bottom of the secondary nozzle disk operatively associated with each liquid outlet, the flap valve being drawn to cover and seal the liquid outlet when the corresponding gas nozzle is closed by a vacuum created by pressurized gas flowing from a recruited nozzle and the flap valve being pushed open when the corresponding gas nozzle is recruited.

21. A nebulizer for providing a select rate of flow of gas entraining a nebulized liquid, the nebulizer comprising:
at least two gas nozzles, each gas nozzle being connectable in fluid communication to a pressurized carrier gas supply;
a liquid outlet corresponding to each gas nozzle, each liquid outlet being connectable in liquid communication with a liquid supply and being positioned proximate to a gas outlet of the corresponding nozzle for nebulization of liquid from the liquid outlet in a stream of carrier gas flowing from the gas outlet of each nozzle; and
a gas valve in fluid communication with at least one of the gas nozzles, the gas valve selectively recruiting the at least one gas nozzle and preventing gas from flowing from the at least one gas nozzle and at least one other of the gas nozzles being independent of the gas valve to provide a continuous flow of gas.

22. The nebulizer of claim 21 further comprising threads in an interior surface of the cylinder, thread engaging means on the plunger and means for preventing the plunger from rotating with the cylinder, whereby relative rotation between the cylinder and the plunger in a first rotational direction will cause the plunger to move lengthwise toward the second end of the cylinder and relative rotation in a second rotational direction will cause the plunger to move lengthwise away from the second end of the cylinder.

23. The nebulizer of claim 21 wherein the gas valve comprises:
a cylinder having first and second ends and a hole through the cylinder wall corresponding to each gas nozzle, each hole being spaced lengthwise along the cylinder wall between the first and second ends;
a conduit connecting each hole to the corresponding nozzle;
a plunger disposed within the cylinder, the plunger having a cylindrical side wall with one end open and the other end closed to define a fluid plenum, the outer diameter of the plunger being less than the inner diameter of the cylinder to define an annular space therebetween, the plunger including an orifice in the side wall between the fluid plenum and outside the fluid plenum, the plunger further including a seal between the closed end and the orifice, the seal forming a fluid tight seal between the interior of the cylinder and the side wall of the plunger, the open end of the plunger being connectable in fluid communication to the pressurized carrier gas supply, the plunger being movable within the cylinder in a first lengthwise direction to recruit select nozzles by moving the sealing means between the hole corresponding to the nozzle and the second end of the cylinder and in a second lengthwise direction to prevent flow to select nozzles by moving the sealing means between the corresponding hole and the first end of the cylinder.

24. The nebulizer of claim 23 further comprising:
a housing having a wall and a mixing chamber within the wall for receiving gas and nebulized liquid from the gas outlet and associated liquid outlets, the wall having at least one ambient air vent for providing a flow of ambient air into the mixing chamber and an outlet for exhausting the nebulized liquid, gas and ambient air;
a collar having a wall enveloping a portion of an outer surface of the housing, the collar including a window for selectively varying the effective size of the ambient air vent between fully open and fully closed by varying the extent to which the window is aligned with the vent; and
a linkage between the collar and the plunger for moving the plunger in the first lengthwise direction as the effective size of the air vent is closed and for moving the plunger in the second lengthwise direction as the effective size of the air vent is opened.

25. The nebulizer of claim 22 further comprising:
a cylindrical housing having a wall and a mixing chamber within the wall for receiving gas and nebulized liquid from the gas outlet and associated liquid outlets, the wall having at least one ambient air vent for providing a flow of ambient air into the mixing chamber and an outlet for exhausting the nebulized liquid, gas and ambient air;
a cylindrical collar having a wall enveloping a portion of an outer surface of the housing, the collar including a window for selectively varying the effective size of the ambient air vent between fully open by rotation of the collar relative to the housing in a first rotational direction to align the window and vent and fully closed by rotation of the collar in a second opposite rotational direction to put the window and vent in an unaligned position; and
a linkage between the cylindrical collar and the plunger for moving the plunger in the second lengthwise direction relative to the cylinder as the cylindrical collar is rotated in the first rotational direction and for moving the plunger in the first direction relative to the cylinder as the cylindrical collar is rotated in the second rotational direction.

26. A nebulizer for providing a select rate of flow of gas entraining a nebulized liquid the nebulizer comprising:
at least two gas nozzles, each gas nozzle being connectable in fluid communication to a pressurized carrier gas supply;
a liquid outlet corresponding to each gas nozzle, each liquid outlet being connectable in liquid communication with a liquid supply and being positioned proximate to a gas outlet of the corresponding nozzle for nebulization of liquid from the liquid outlet in a stream of carrier gas flowing from the gas outlet of each nozzle;

a gas valve in fluid communication with at least one of the gas nozzles, the gas valve selectively recruiting the at least one gas nozzle and preventing gas from flowing from the at least one gas nozzle; and a liquid control valve in liquid communication with each liquid outlet, the liquid control valve selectively allowing and preventing flow of liquid through a select liquid outlet.

27. The nebulizer of claim 26 further comprising a coordinator between the liquid control valve and the gas valve, the coordinator actuating the liquid control valve to prevent flow of liquid through a liquid outlet when the gas valve selectively prevents gas from flowing from a corresponding gas nozzle and for actuating the liquid control valve to allow flow of liquid through a liquid outlet when the gas valve selectively recruits a corresponding gas nozzle.

28. The nebulizer of claim 27 comprising a plurality of gas nozzles and a corresponding plurality of liquid outlets, each liquid outlet positioned proximate to a distinct gas nozzle to define liquid outlet gas nozzle pairs, the coordinator coordinating gas and liquid flow through the liquid outlet gas nozzle pairs.

29. The nebulizer of claim 27 further comprising:

a housing having a wall and a mixing chamber within the wall for receiving gas and nebulized liquid from the gas outlet and corresponding liquid outlets, the wall having at least one ambient air vent for providing a flow of ambient air into the mixing chamber and an outlet for exhausting the nebulized liquid, gas and ambient air;

a vent valve operatively associated with the ambient air vent, the vent valve selectively varying the effective size of the ambient air vent between fully open and fully closed; and a linkage between the gas valve and the vent valve, the linkage automatically increasing the number of nozzles recruited by the gas valve as the vent valve is adjusted to decrease the effective size of the vent and the linkage automatically decreasing the number of nozzles recruited by the gas valve as the vent valve is adjusted to increase the effective size of the vent.

30. A nebulizer for providing a select rate of flow of gas entraining a nebulized liquid, the nebulizer comprising:

at least two gas nozzles, each gas nozzle being connectable in fluid communication to a pressurized carrier gas supply;

a liquid outlet corresponding to each gas nozzle, each liquid outlet being connectable in liquid communication with a liquid supply and being positioned proximate to a gas outlet of the corresponding nozzle for nebulization of liquid from the liquid outlet in a stream of carrier gas flowing from the gas outlet of each nozzle;

a gas valve in fluid communication with at least one of the gas nozzles, the gas valve selectively recruiting the at least one gas nozzle and preventing gas from flowing from the at least one gas nozzle; and a housing having a wall and a mixing chamber within the wall for receiving gas and nebulized liquid from the gas outlets and corresponding liquid outlets, the wall having at least one ambient air vent for providing a flow of ambient air into the mixing chamber and an outlet for exhausting the nebulized liquid, gas and ambient air.

31. The nebulizer of claim 30 further comprising a vent valve operatively associated with the ambient air vent, the vent valve selectively varying the effective size of the ambient air vent between fully open and fully closed.

32. The nebulizer of claim 31 further comprising a linkage between the gas valve and the vent valve, the linkage automatically increasing the number of nozzles recruited by the gas valve as the vent valve is adjusted to decrease the effective size of the vent and the linkage automatically decreasing the number of nozzles recruited by the gas valve as the vent valve is adjusted to increase the effective size of the vent.

* * * * *